United States Patent
Coleman et al.

(10) Patent No.: US 8,197,498 B2
(45) Date of Patent: Jun. 12, 2012

(54) GASTRIC BYPASS DEVICES AND PROCEDURES

(75) Inventors: James E. Coleman, Terenure (IE); Christy Cummins, Naas (IE)

(73) Assignee: Trinitas Ventures Ltd., Dublin (IE)

( * ) Notice: Subject to any disclaimer, the term of this patent is extended or adjusted under 35 U.S.C. 154(b) by 474 days.

(21) Appl. No.: 12/266,174

(22) Filed: Nov. 6, 2008

(65) Prior Publication Data

US 2010/0114128 A1    May 6, 2010

(51) Int. Cl.
    *A61B 17/08*      (2006.01)
(52) U.S. Cl. ......................... 606/153; 606/151; 606/142
(58) Field of Classification Search ................. 606/139, 606/142, 151, 153, 155
See application file for complete search history.

(56) References Cited

U.S. PATENT DOCUMENTS

| | | | |
|---|---|---|---|
| 3,942,407 A | 3/1976 | Mortensen | |
| 5,035,702 A | 7/1991 | Taheri | |
| 5,197,971 A | 3/1993 | Bonutti | |
| 5,222,963 A * | 6/1993 | Brinkerhoff et al. | 606/153 |
| 5,342,393 A | 8/1994 | Stack | |
| 5,496,332 A | 3/1996 | Sierra et al. | |
| 5,741,297 A | 4/1998 | Simon | |
| 5,853,422 A | 12/1998 | Huebsch et al. | |
| 6,024,756 A | 2/2000 | Huebsch et al. | |
| 6,117,159 A | 9/2000 | Huebsch et al. | |
| 6,183,496 B1 | 2/2001 | Urbanski | |
| 6,190,353 B1 * | 2/2001 | Makower et al. | 604/95.01 |
| 6,261,309 B1 | 7/2001 | Urbanski | |
| 6,312,446 B1 | 11/2001 | Huebsch et al. | |
| 6,355,052 B1 | 3/2002 | Neuss et al. | |
| 6,375,671 B1 | 4/2002 | Kobayashi et al. | |
| 6,461,320 B1 | 10/2002 | Yencho et al. | |
| 6,616,685 B2 | 9/2003 | Rousseau | |
| 6,623,508 B2 | 9/2003 | Shaw et al. | |
| 6,776,785 B1 | 8/2004 | Yencho et al. | |

(Continued)

FOREIGN PATENT DOCUMENTS

EP    1908419 A1    4/2008

(Continued)

OTHER PUBLICATIONS

International Search Report and Written Opinion Application No. PCTEP2008008178 dated Aug. 6, 2009, 23 pgs.

(Continued)

*Primary Examiner* — Corrine M McDermott
*Assistant Examiner* — Alexander Orkin
(74) *Attorney, Agent, or Firm* — Nutter McClennen & Fish LLP

(57) ABSTRACT

Methods and devices for treating obesity are provided, and more particularly, methods and devices for performing gastric bypasses are disclosed. In one exemplary embodiment a gastric bypass procedure is provided that includes forming a gastro-entero anastomosis between a stomach and an intestine and forming an entero-entero anastomosis between a portion of the intestine distal to the gastro-entero anastomosis and a portion of the intestine proximal to the gastro-entero anastomosis. A surrogate path is formed between the esophagus and the gastro-entero anastomosis to at least partially direct fluid from the esophagus to the intestine by way of the gastro-entero anastomosis, thereby bypassing the stomach. Devices useful in gastric bypass procedures that include anastomotic devices coupled to or integrally formed with a shunt. The devices can include a plurality of tubular bodies that are configured to have an adjustable length.

26 Claims, 18 Drawing Sheets

U.S. PATENT DOCUMENTS

| | | |
|---|---|---|
| 6,942,674 B2 | 9/2005 | Belef et al. |
| 6,960,224 B2 | 11/2005 | Marino et al. |
| 7,018,388 B2 | 3/2006 | Yencho et al. |
| 7,022,127 B2 | 4/2006 | Suyker et al. |
| 7,108,702 B2 | 9/2006 | Yencho et al. |
| 7,149,587 B2 | 12/2006 | Wardle et al. |
| 7,608,086 B2 * | 10/2009 | Tanaka et al. .................. 606/153 |
| 7,625,392 B2 * | 12/2009 | Coleman et al. ................ 606/213 |
| 7,803,195 B2 * | 9/2010 | Levy et al. ................ 623/23.68 |
| 7,833,280 B2 * | 11/2010 | Stack et al. ................ 623/23.65 |
| 7,846,174 B2 * | 12/2010 | Baker et al. .................... 606/191 |
| 7,892,214 B2 * | 2/2011 | Kagan et al. .................. 604/264 |
| 2002/0183768 A1 * | 12/2002 | Deem et al. .................... 606/151 |
| 2003/0158578 A1 * | 8/2003 | Pantages et al. .............. 606/213 |
| 2003/0171774 A1 | 9/2003 | Freudenthal et al. |
| 2004/0116992 A1 | 6/2004 | Wardle et al. |
| 2004/0122456 A1 | 6/2004 | Saadat et al. |
| 2004/0243155 A1 | 12/2004 | Yencho et al. |
| 2005/0043759 A1 | 2/2005 | Chanduszko |
| 2005/0055050 A1 | 3/2005 | Alfaro |
| 2005/0070935 A1 | 3/2005 | Ortiz |
| 2005/0075665 A1 | 4/2005 | Brenzel et al. |
| 2005/0149071 A1 | 7/2005 | Abbott et al. |
| 2005/0251209 A1 | 11/2005 | Saadat et al. |
| 2005/0267524 A1 | 12/2005 | Chanduszko |
| 2005/0273124 A1 | 12/2005 | Chanduszko |
| 2005/0277966 A1 | 12/2005 | Ewers et al. |
| 2005/0288786 A1 * | 12/2005 | Chanduszko .............. 623/11.11 |
| 2006/0190036 A1 | 8/2006 | Wendel et al. |
| 2006/0196137 A1 | 9/2006 | Brenzel et al. |
| 2006/0211999 A1 | 9/2006 | Fangrow |
| 2006/0217748 A1 | 9/2006 | Ortiz |
| 2006/0265004 A1 | 11/2006 | Callaghan et al. |
| 2007/0021758 A1 | 1/2007 | Ortiz |
| 2007/0185529 A1 | 8/2007 | Coleman et al. |
| 2007/0233162 A1 * | 10/2007 | Gannoe et al. ................ 606/153 |
| 2008/0147101 A1 * | 6/2008 | Ortiz et al. ..................... 606/153 |
| 2009/0105733 A1 | 4/2009 | Coleman et al. |
| 2010/0004681 A1 | 1/2010 | Coleman et al. |
| 2010/0256673 A1 | 10/2010 | Coleman et al. |

FOREIGN PATENT DOCUMENTS

| | | |
|---|---|---|
| WO | 0009040 A1 | 2/2000 |
| WO | 0149185 | 7/2001 |
| WO | 0205718 A2 | 1/2002 |
| WO | WO-03034927 A1 | 5/2003 |
| WO | 2007013070 A1 | 2/2007 |
| WO | 2007073566 A1 | 6/2007 |
| WO | 2008040577 A1 | 4/2008 |

OTHER PUBLICATIONS

Form PCT/ISA/206 for Application No. PCT/EP2008/008178 dated Mar. 10, 2009, 6 pgs.

International Preliminary Report on Patentability and Written Opinion of the ISA dated Apr. 27, 2010, 13 pgs.

U.S. Appl. No. 11/876,131, filed Oct. 22, 2007.

Examiner Communication from the European Patent Office dated Apr. 30, 2009.

Office Action dated Dec. 16, 2008 issued for U.S. Appl. No. 11/307,372.

Office Action dated Apr. 29, 2009 issued for U.S. Appl. No. 11/307,372.

International Application No. PCTEP2008008178 Search Report dated Jun. 8, 2009, 23 pgs.

Office Action dated Jul. 8, 2009 issued for U.S. Appl. No. 11/307,372.

* cited by examiner

*FIG. 17*          *FIG. 18*
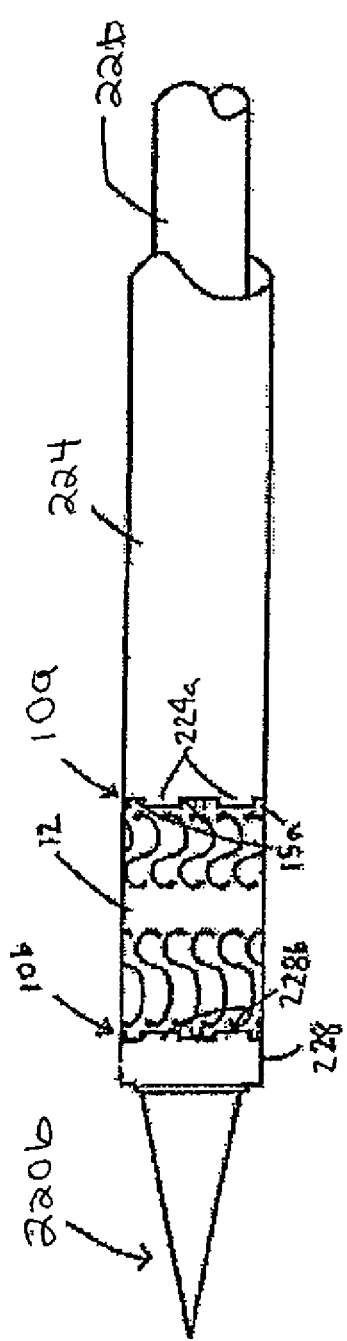

GASTRIC BYPASS DEVICES AND PROCEDURES

FIELD

The present application relates to surgical procedures, and more particularly to methods for performing a gastric bypass.

BACKGROUND

The percentage of the world population suffering from morbid obesity is steadily increasing. Some estimates show the number of people that suffer from morbid obesity in the United States alone exceeds 10 million, and the deaths of an estimated 500,000 people could be related to obesity. Severely obese people are susceptible to an increased risk of many medical conditions, including heart disease, stroke, diabetes, pulmonary disease, hypertension, gall bladder disease, osteoarthritis, sleep apnea and other breathing problems, some forms of cancer (e.g., uterine, breast, colorectal, kidney, and gall bladder), accidents, and death.

Surgical treatment options for treating obesity are growing and being performed at an increasing rate. These approaches can generally be categorized as either malabsorptive or restrictive. Absorptive procedures modify the gastrointestinal tract so that only a small fraction of the food and fluid intake is actually digested; restrictive procedures limit an amount of food and fluid intake. Following a restrictive procedure, a patient's ability to eat is severely restricted. The patient can only eat a limited amount of food and fluid and any attempt to eat more will result in varying degrees of discomfort.

A leading surgical approach for treating obesity is often referred to as the Roux-en-Y gastric bypass procedure. A Roux-en-Y procedure combines restrictive and malabsorptive approaches by restricting the stomach and bypassing a proximal portion of the small intestine. The stomach is typically restricted by stapling at least a portion of the stomach to create a pouch, effectively limiting the size of a patient's stomach and thereby limiting a patient's food and fluid intake. Staple line failures, however, are a known problem of Roux-en-Y gastric bypass procedures. When a staple line fails, the patient can regain weight. It also can cause the body to be exposed to undesirable outside materials, such as stray staples. To prevent staple line failure, some surgeons practice additional techniques to make the division more secure, for example by suturing off the pouch from the portion of the stomach that is to remain a part of the digestive tract. The creation of pouches, however, is not generally desirable because they can result in stenosis, e.g., stricture of the stomach stoma that can have a major effect on a patient's eating, and dilation, e.g., stretching of the stomach that can result in weight gain. It is currently believed that about 5 to 10 percent of Roux-en-Y patients have dilation problems and about 2 percent have intestinal obstruction. Further, metabolic complications can also occur following a Roux-en-Y procedure, such as anemia and calcium deficiency, because essential vitamins and nutrients of blood production (e.g., iron and vitamin B12) depend on the stomach and intestine for absorption, and because calcium is best absorbed in the duodenum, which is bypassed in a Roux-en-Y procedure. Still further, current procedures like Roux-en-Y are difficult to adjust and impossible to reverse, despite the fact that it can be desirable to make adjustments to the gastric bypass for the patient or even reverse the gastric bypass entirely.

It is thus desirable to provide a new surgical procedure for treating obesity that does not create pouches in the stomach, does not use staples, and which can be easily adjusted or even reversed.

Further, mitral regurgitation is the most prevalent form of valvular heart disease. Surgical therapy for mitral valve regurgitation is common with approximately 20,000 procedures performed in the United States each year. Operative strategies and techniques have progressed significantly since the early experience with emphasis on mitral valve repair instead of replacement. Subsequently, the mortality rate for surgical mitral valve repair is now less than 5% and lasting results (freedom from re-operation), particularly when treating primary mitral regurgitation are reported to be greater than 90% at five years at follow-up. Recently, a new paradigm has emerged for the treatment of mitral regurgitation. This is based on percutaneous techniques and the experiences of both cardiac surgeons and interventional cardiologists.

It is thus also desirable to provide new surgical procedures for repairing a heart valve.

SUMMARY

The present invention generally provides methods for treating obesity. In one embodiment, a method for forming a gastric bypass includes forming an anastomosis between first and second portions of an intestine, e.g., an entero-entero anastomosis, to form a loop in the intestine, forming an anastomosis between the loop and the stomach, e.g., a gastro-entero anastomosis, and implanting a shunt in the stomach. The shunt is generally configured to at least partially direct a fluid passing therethrough from the esophagus through the gastro-entero anastomosis. The fluid can be directed in a number of different directions upon passing through the gastro-entero anastomosis, including to only a first portion of the loop that is proximal to the gastro-entero anastomosis, to only a second portion of the loop that is distal to the gastro-entero anastomosis, or to both the first and second portions of the loop. An anastomotic device can be implanted in either or both the gastro-entero anastomosis and the entero-entero anastomosis. The anastomotic device can include a connector, and the method can include adjusting a length of the connector extending between a proximal end and a distal end of the anastomotic device. The length can be adjusted in a variety of ways, for example, by rotating a rod disposed between the proximal and distal ends of the anastomotic device. In one embodiment, the anastomotic device includes a proximal tubular body and a distal tubular body, and a length of the connector can be adjusted by positioning the proximal tubular body along a portion of the distal tubular body. Further, implanting one or more anastomotic devices can be performed in a variety of ways, but in one embodiment implanting the device can include coupling an anastomotic device to at least a portion of an actuator that is used to deploy the anastomotic device using sutures. In another embodiment, implanting the anastomotic device can include coupling the device to at least a portion of an actuator that is used to deploy the anastomotic device by locking the anastomotic device to the actuator. In still another embodiment, implanting the anastomotic device can include breaking apart a portion of an actuator used to deploy the anastomotic device to remove the actuator from the anastomotic device. The shunt can be configured to pass through the anastomotic device at the gastro-entero anastomosis, or alternatively, the shunt can include an anastomotic device integrally formed thereon. Further, implanting the shunt can include inserting an endoscope through the shunt and manipulating the endoscope to advance a delivering shaft coupled to the shunt along a tortuous pathway. The shunt can include a one-way valve that is configured to inhibit acid reflux.

In one embodiment the gastro-entero anastomosis can be formed prior to forming the entero-entero anastomosis. In such an embodiment, an anastomosis-forming device can be passed through the gastro-entero anastomosis to form the entero-entero anastomosis. In another embodiment the entero-entero anastomosis can be formed prior to forming the gastro-entero anastomosis. In such an embodiment, an anastomosis-forming device can be used to form the gastro-entero anastomosis prior to removing the anastomosis-forming device from the surgical site. The gastric bypass can also be reversed, for example, by removing the shunt.

In another embodiment of a method for forming a gastric bypass, a portion of an intestine can be positioned adjacent to a stomach and a fluid connection can be formed therebetween. A surrogate path from an esophagus to a distal portion of the intestine, by way of the connection between the portion of the intestine and the stomach, can be formed such that fluid is at least partially directed from the esophagus to the intestine through the connection. The formation of the surrogate path allows the stomach to be bypassed. The method can also include forming a connection between the distal portion of the intestine and a proximal portion of the intestine, which is the portion of the intestine proximal to the connection between the stomach and the intestine. The surrogate path can extend to the proximal portion of the intestine, in addition to or in lieu of extending to the distal portion of the intestine, by way of the connection between the intestine and the stomach. The connection between the stomach and the intestine can be formed by implanting a first anastomotic device therebetween. The connection between the proximal and the distal portions of the intestine can be formed by advancing a second anastomotic device through the first anastomotic device and implanting the second anastomotic device between the proximal and distal portions of the intestine. The surrogate path can be formed by implanting a shunt to extend between the esophagus and the connection between the stomach and the intestine. The shunt can be implanted, for example, by transorally advancing an endoscope having a delivery shaft coupled to the shunt disposed therearound. In one embodiment the shunt includes an anastomotic device formed thereon that can be implanted between the stomach and the intestine to form the fluid connection therebetween. The gastric bypass can be reversed, for example, by removing the surrogate path.

In another embodiment of a method for treating obesity an elongate member can be implanted in the stomach such that the elongate member extends from the esophagus and through an anastomosis formed between the stomach and an intestine. The elongate member can at least partially divert fluid from the esophagus to the intestine, which in turn bypasses the stomach and at least a portion of the intestine proximal to the anastomosis. The method can further include forming a second anastomosis between a proximal portion of the intestine, which is the portion of the intestine proximal to the anastomosis formed between the stomach and the intestine, and a distal portion of the intestine, which is the portion of the intestine distal to the anastomosis formed between the stomach and the intestine. The method for treating obesity can be reversed, for example, by removing the elongate member.

The present invention also provides for a variety of anastomotic devices that can be used to help form anastomoses. In one embodiment of an anastomotic device, the device includes a first tubular body and a second tubular body. The first tubular body can include a proximal end and a distal end, and the distal end can be adapted to expand upon rotation to form distal wings. The second tubular body can include a distal end that can be slidably coupled to the proximal end of the first tubular body and a proximal end that can be adapted to expand upon rotation to form proximal wings that extend toward the distal wings of the first tubular body to engage tissue therebetween. The distal end of the first tubular body and the proximal end of the second tubular body can include a plurality of asymmetrical substantially s-shaped slits that are formed therein. Further, the first and second tubular bodies can each include a lumen formed therethrough such that the lumens are configured to form a passageway through tissue. In one embodiment each of the first and second tubular bodies are formed from a non-permeable material. The first and second tubular bodies can be configured such that they form a shunt. The shunt can include a proximal end that is adapted to receive a fluid and a distal end that is configured to direct fluid in a single direction, or alternatively, in a plurality of directions.

In another embodiment of an anastomotic device, the device can include a first tubular body and a second tubular body. The first tubular body can include an elongate proximal end and a distal end that is adapted to expand upon rotation to form distal wings. The second tubular body can include a proximal end that is adapted to expand upon rotation to form proximal wings that extend toward the distal wings of the first tubular body to engage tissue therebetween and a distal end that is adapted to be selectively positioned along the elongate proximal end of the first tubular body. The distal end of the first tubular body and the proximal end of the second tubular body can include a plurality of asymmetrical substantially s-shaped slits formed therein. Further, the first and second tubular bodies can each include a lumen formed therethrough such that the lumens are configured to form a passageway through tissue. In one embodiment each of the first and second tubular bodies are formed from a non-permeable material. The first and second tubular bodies can be configured such that they form a shunt. The shunt can include a proximal end that is adapted to receive a fluid and a distal end that is configured to direct fluid in a single direction, or alternatively, in a plurality of directions.

The present invention also includes methods for repairing an abdominal aortic aneurysm. In one exemplary embodiment, the method includes positioning a dome over a fenestration in an aorta to place an anastomotic device coupled to a first artery in fluid communication with a second artery disposed on an opposite site of the aorta. The method can further include placing a vascular conduit having a fenestration in the aorta such that the dome is positioned over the fenestration in the vascular conduit.

BRIEF DESCRIPTION OF DRAWINGS

This invention will be more fully understood from the following detailed description taken in conjunction with the accompanying drawings, in which:

FIG. 17 is a side view of the anastomotic device of FIG. 16 and a distal portion of the actuator of FIG. 16;

FIG. 18 is a cross-sectional view of the anastomotic device and the inner shaft of FIG. 17;

DETAILED DESCRIPTION

Figure 1:
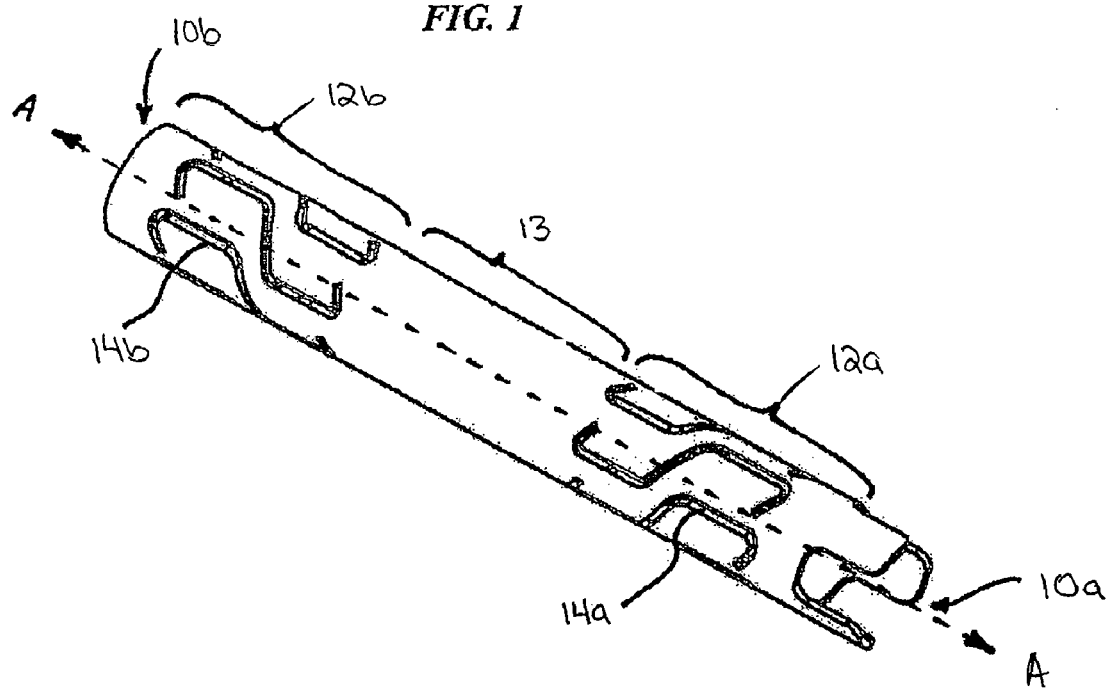
FIG. 1 is a side view of one exemplary embodiment of an anastomotic device in an initial, unformed configuration.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides methods and devices for treating obesity by way of a gastric bypass procedure. The methods generally involve the formation of a surrogate path that extends between a patient's esophagus and an anastomosis formed between the patient's stomach and intestine. In an exemplary embodiment, the surrogate path can be formed with a shunt that is effective to allow fluid that passes therethrough to bypass the patient's stomach. The term fluid is used herein to generally refer to any material that can pass through a patient's esophagus, including but not limited to food, liquid, and other materials that can pass through a digestive system. The disclosed methods are particularly advantageous as they do not involve stapling or any other sectioning off of one portion of the stomach from another such that only a portion of the stomach receives fluid. The methods are also reversible to completely eliminate the gastric bypass based on the needs of the patient. The present methods are particularly conducive to Natural Orifice Translumenal Endoscopic Surgery (NOTES) procedures, making the procedure less painful for patients, although other types of procedures, such as laparoscopic and open procedures, can also be used to perform the present methods.

As indicated above, in general the disclosed methods for forming a gastric bypass can include forming at least one anastomosis. The anastomosis can be formed in a variety of different ways using a variety of instruments. Because an anastomosis involves joining two spaces that are not normally connected to allow fluid to flow therethrough, various tools and implants known in the art can be used to form the anastomosis. Exemplary embodiments of anastomotic devices and methods for forming anastomoses are disclosed in U.S. patent application Ser. No. 11/876,131 of Coleman et al., filed on Oct. 22, 2007, and entitled "Anastomotic devices and Methods," (hereinafter "the '131 Application") which is hereby incorporated by reference in its entirety.

FIGS. 1-5 illustrate one exemplary embodiment of an anastomotic device 10 that can be used to form an anastomosis. As shown, the device 10 is in the form of a generally elongate tubular body 12 with an open proximal end 10a and an open distal end 10b. The device 10 further includes proximal and distal portions 12a, 12b that are configured to expand to engage tissue therebetween. As illustrated in the un-deployed device 10 of FIG. 1, the proximal and distal portions 12a, 12b each include a plurality of slits 14a, 14b formed therein and configured to allow portions of the elongate tubular body 12 between the plurality of slits 14a, 14b to radially expand. A mid-portion 13 of the tubular body 12, located between the proximal and distal portions 12a, 12b, can be configured to be positioned between two cut body lumens, e.g., within an anastomosis. The mid-portion 13 can have a fixed or adjustable length that corresponds to a thickness of the tissue walls. When implanted, the device 10 is generally configured to form a solid connection between two distinct spaces within the body, e.g., the stomach and the intestine or two portions of the intestine.

The slits 14a, 14b in the proximal and distal portions 12a, 12b can extend in any direction, and each portion 12a, 12b can include any number of slits. Preferably, the slits 14a, 14b are configured such that certain portions of the elongate tubular body 12 between the slits 14a, 14b will extend outward away from a central axis A of the tubular body 12 when the body 12 is axially compressed, and preferably rotated as well. As a result, one or more wings will form in each of the distal and proximal portions 12a, 12b to engage tissue therebetween. The device 10 can also include tabs 15a in the proximal portion 12a to aid in forming the wings, as discussed further below. Tabs can likewise be formed in distal portion 12b if desired. In an exemplary embodiment, as shown in FIG. 1, the slits 14a, 14b are substantially S-shaped. The slits 14a, 14b can extend longitudinally along the elongate tubular body 12 in a proximal-distal direction, and they can be spaced axially around the elongate tubular body 12. More preferably, the slits 14a in the distal portion 12a can extend in a first direction around a circumference of the elongate tubular body 12 and the slits 14b in the proximal portion 12b can extend in a second, opposite direction around the circumference of the elongate tubular body 12. Such a configuration allows the tubular body 12 to be rotated in a first direction to cause only one of the proximal and distal portions 12a, 12b to radially expand, and then to be rotated in a second direction to cause the other one of the proximal and distal portions 12a, 12b to radially expand.

Figure 2:
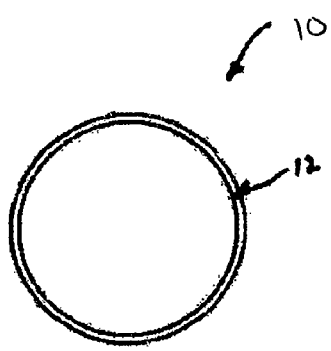
FIG. 2 is an end view of the anastomotic device of FIG. 1 prior to deployment.
Figure 3:
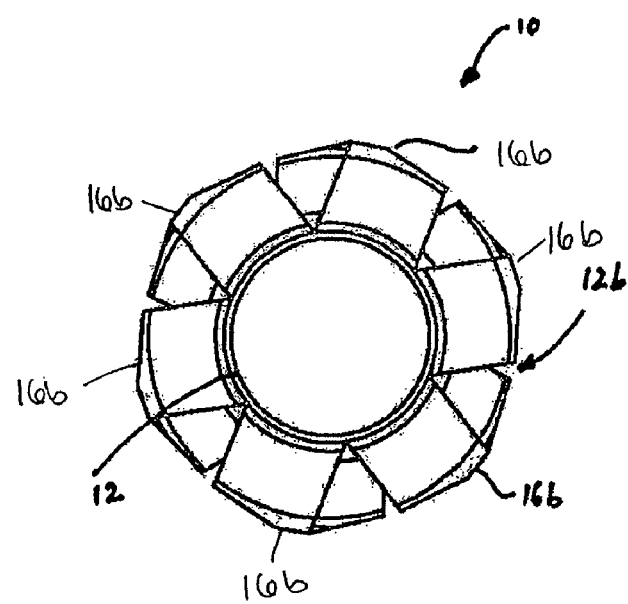
FIG. 3 is an end view of the anastomotic device of FIG. 1 following deployment.

FIGS. 2 and 3 show distal end views of the device 10 in its pre-deployed configuration and following partial or full deployment, respectively. In the pre-deployed configuration shown in FIG. 2, the elongate tubular body 12 has a diameter that is configured to fit within a body lumen in tissue, e.g., through an opening in the stomach and/or in the intestine, and that may be configured to fit within an introducer sheath for guiding the device 10 to an anastomotic site. FIG. 3 illustrates the distal portion 12b radially expanded to form the distal wings. When the proximal portion 12a is radially expanded to form the proximal wings, the proximal wings can be aligned with the distal wings to facilitate lumen joining. In such a case, the distal end view of the device 10 would look as shown in FIG. 3 both before and after deployment of the proximal wings. The proximal wings can also be offset radially from the distal wings. In the illustrated embodiment, the slits 14a, 14b are configured such that the proximal and distal portions 12a, 12b each include six wings, however the proximal and distal portions can include any number of wings.

Figure 4:
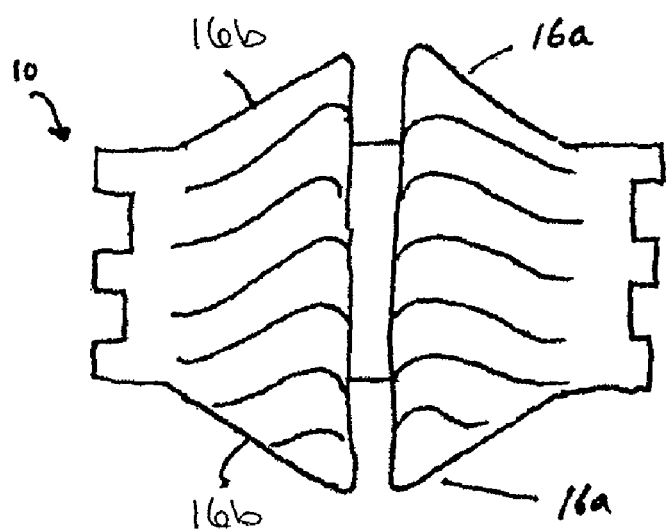
FIG. 4 is a side view of the anastomotic device of FIG. 1 following deployment.

FIG. 4 shows the anastomotic device 10 in a deployed configuration. In the deployed configuration, the proximal portion 12a is expanded to form proximal wings 16a, and the distal portion 12b is expanded to form distal wings 16b. The wings 16a, 16b are formed by the material between the slits 14a, 14b, which is deformed outward as the outer elongate body 12 is compressed and preferably rotated. The wings 16a, 16b can be concurrently or sequentially formed, e.g., deploying the distal wings 16b before the proximal wings 16a.

Figure 5:
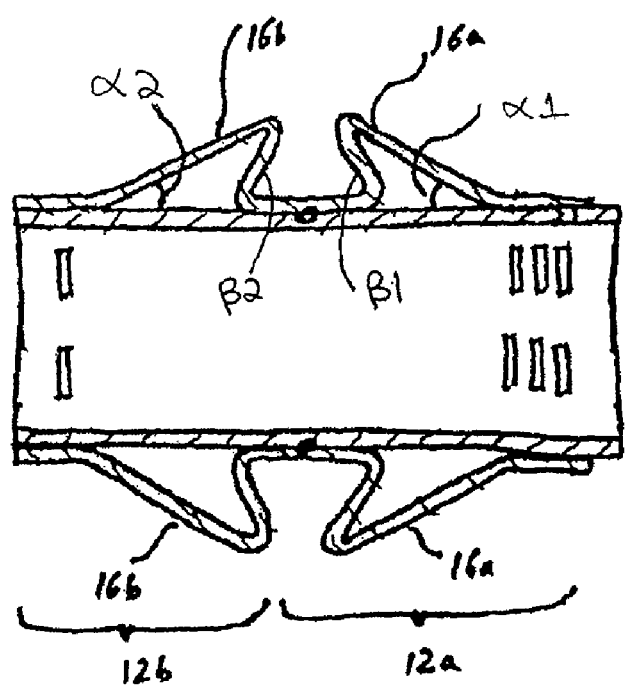
FIG. 5 is a cross-sectional view of the anastomotic device of FIG. 4 following deployment.
Figure 6:
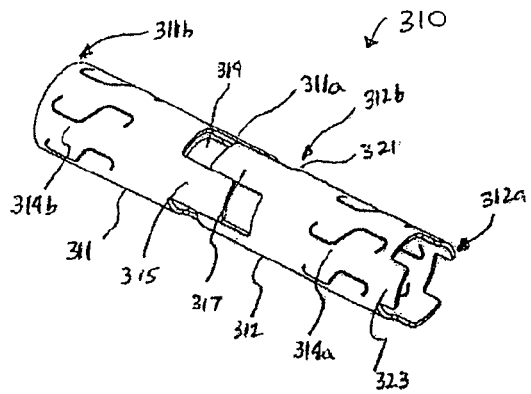
FIG. 6 is a perspective view of another exemplary embodiment of an anastomotic device in an initial, unformed configuration.

FIG. 5 shows a cross-sectional view of the deployed device 10 of FIG. 4. The asymmetric profile of the slits 14a, 14b can allow the wings 16a, 16b to form such that interior base bend angles α1, α2 are less than respective exterior base bend angles β1, β2. As a result, the wings 16a, 16b will also extend toward one another. The interior based bend angles α1, α2 can be the same or different in the proximal and distal portions 12a, 12b, as can the exterior base bend angles β1, β2. If the exterior base bend angles β1, β2 are each about 90 degrees, the wings 16a, 16b extend substantially parallel to each other, while acute and obtuse exterior base bend angles β1, β2 can allow the wings 16a, 16b to be angled toward each other at one end and away from each other at the opposite end.

The tubular body 12 can be formed from a variety of materials including absorbable and non-absorbable materials. In an exemplary embodiment, the device 10 is formed from a deformable material that undergoes plastic deformation (i.e., deformation with negligible elastic component). Exemplary materials include, by way of non-limiting example, any resorbable (e.g., biocompatible and/or bioabsorbable) materials, including, for example, titanium (and titanium alloys), magnesium alloys, stainless steel, polymeric materials (synthetic and/or natural), shape memory material such as nitinol, ceramic, etc. Materials which are not normally radiopaque, e.g., magnesium alloy, may be enhanced and made x-ray visible with the addition of x-ray visible materials, such as particles of iron oxide, stainless steel, titanium, tantalum, platinum, or any other suitable equivalents. Further, the materials discussed below with respect to the shunts can also be used to form and/or coat the tubular body 12, including non-permeable materials, such as polyethylene terephthalate and polyvinylidene chloride, and semi-permeable materials, such as polylactide.

Figure 7:
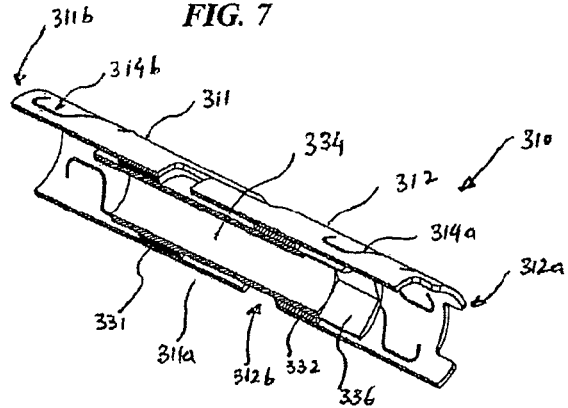
FIG. 7 is a perspective cross-sectional view of the anastomotic device of FIG. 6.
Figure 8:
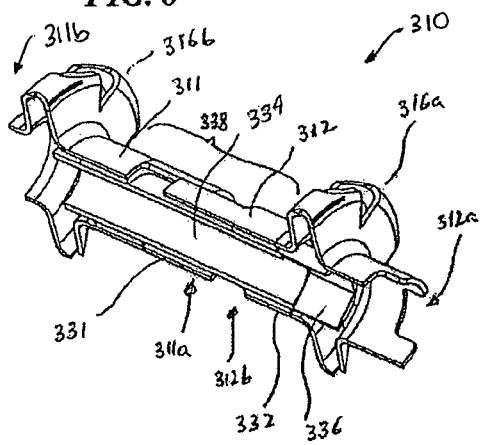
FIG. 8 is a perspective cross-sectional view of the anastomotic device of FIG. 6 following deployment.
Figure 9:
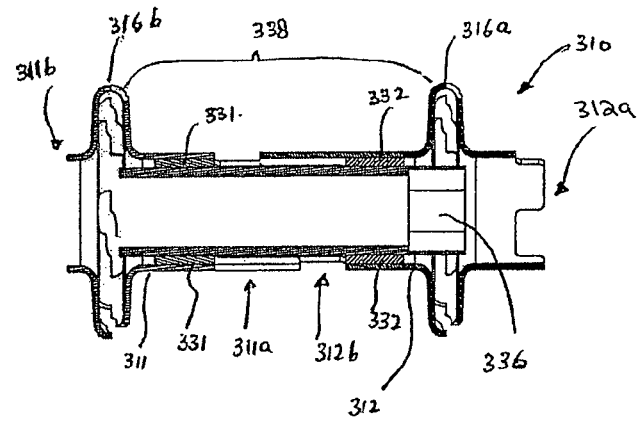
FIG. 9 is a side cross-sectional view of the anastomotic device of FIG. 8 following deployment.
Figure 10:
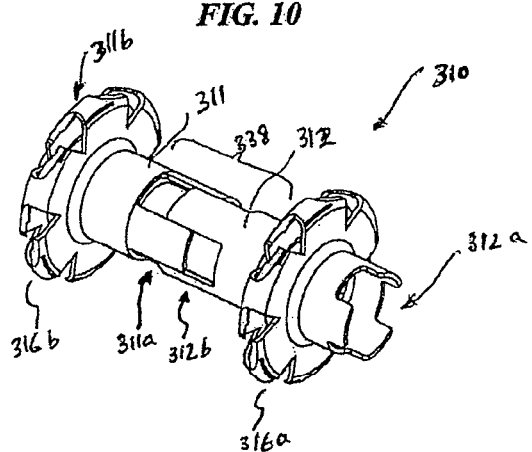
FIG. 10 is a perspective view of the anastomotic device of FIG. 6 following deployment.
Figure 11:
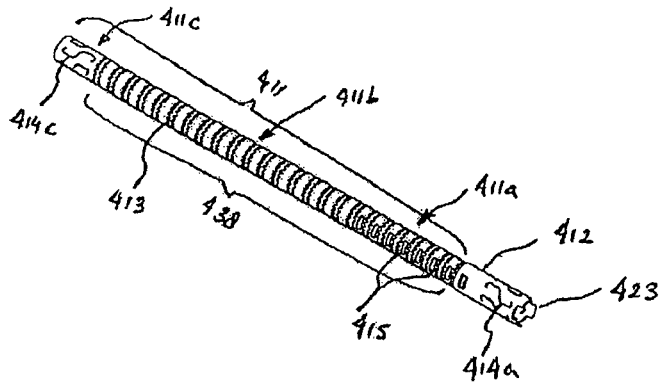
FIG. 11 is a perspective view of another exemplary embodiment of an anastomotic device in an initial, unformed configuration.

FIGS. 6-10 illustrate another exemplary embodiment of an anastomotic device 310 that can be used to form an anastomosis. The device 310 is configured to have an adjustable length. As shown, the device 310 is in the form of two separate elongated tubular bodies 311, 312, with open proximal ends 311a, 312a and open distal ends 311b, 312b. The proximal end 311a of tubular body 311 can be configured to couple with the distal end 312b of tubular body 312, while the distal end 311b of tubular body 311 and the proximal end 312a of tubular body 312 can be configured to expand to engage tissue therebetween. As illustrated in the un-deployed device 310 of FIG. 6, the distal end 311b and the proximal end 312a each include a plurality of slits 314b, 314a, respectively, formed therein and configured to allow portions of the respective elongate tubular bodies 311, 312 between the plurality of slits 314b, 314a to radially expand. In the illustrated embodiment the slits 314a, 314b are substantially S-shaped to expand in a radial direction and form wings 316b, 316a, as shown in FIGS. 8-10. As also illustrated in the un-deployed device 310 of FIG. 6, the proximal end 311a and the distal end 312b each include a plurality of tabs 315, 317, respectively. Disposed between each of tabs 315, 317 are notches 319, 321, respectively. The tabs 315, 317 can be configured to mate within the notches 319, 321 of the respective tubular bodies 311, 312 as shown, thereby forming an interlocking relationship between the tubular bodies 311, 312. The notches 319, 321 allow the tabs 315, 317 to slide axially within the notches 319, 321, which in turn allows the tubular bodies 311, 312 to slide axially relative to each other to provide a variable length. In one embodiment, the proximal end 312a of the tubular body 312 includes tabs 323 to assist with the introduction of the tubular bodies 311, 312 to the anastomosis. A person having ordinary skill in the art would recognize that in other embodiments tabs 323 can be formed in the tubular body 311 in a similar manner for a similar purpose. Further, a person having ordinary skill in the art would recognize that the tubular bodies 311, 312 can be coupled together in a variety of ways that allow for the tubular bodies 311, 312 to slide axially to provide a variable length, and that such ways can be used to couple the tubular bodies 311, 312 together. In some embodiments, three or more tubular embodiments may be desirable. Although bodies 311, 312 are discussed as being tubular, a person having ordinary skill in the art would recognize that other shapes can also be used to form the bodies 311, 312.

As seen in FIGS. 7-9, a threaded insert 331, 332 can be disposed within each tubular body 311, 312, respectively. In one embodiment threaded insert 331 is a left-hand threaded insert and threaded insert 332 is a right-hand threaded insert. Both inserts 331, 332 can be coupled to the respective tubular bodies, for example by welding. A link rod 334 can be disposed within the threaded inserts 331, 332 and it can be configured to integrate the tubular bodies 311, 312. More particularly, the link rod 334 can include threads that correspond to the respective threads of the inserts 331, 332 such that movement of the tubular bodies 311, 312 are restricted. A key 336 can be disposed on one end of the link rod 334 and it can be any shape, but in the illustrated embodiment the key 336 is hexagonal. The key 336 can be engaged externally by a shaft of an agreeable shape to rotate the link rod 334 clockwise or counter-clockwise as desired to adjust a gap 338 of the device 310. More particularly, the threads of the inserts 331, 332 are configured to allow the tubular bodies 311, 312 to move toward each other when the key 336 is rotated in one direction, thereby decreasing the size of the gap 338, and away from each other when the key 336 is rotated in a second direction, thereby increasing the size of the gap 338. FIG. 10 illustrates the device 310 in its final form. In particular, the wings 316a, 316b of the tubular bodies 311, 312 have been deployed and the gap 338 adjusted to a desired length.

Figure 12:
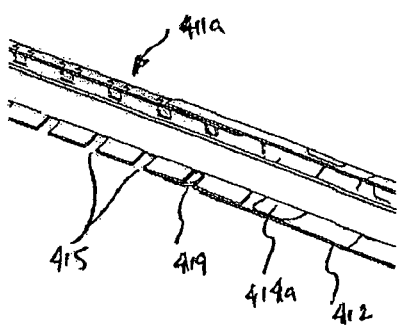
FIG. 12 is a perspective cross-sectional view of the anastomotic device of FIG. 11.
Figure 13:
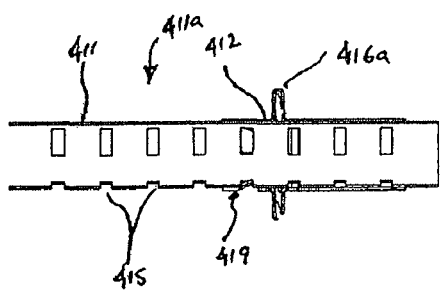
FIG. 13 is a side cross-sectional view of the anastomotic device of FIG. 11.
Figure 14:
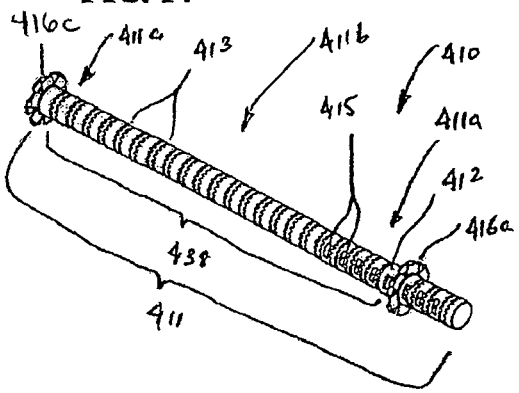
FIG. 14 is a perspective view of the anastomotic device of FIG. 11 following deployment.
Figure 15:
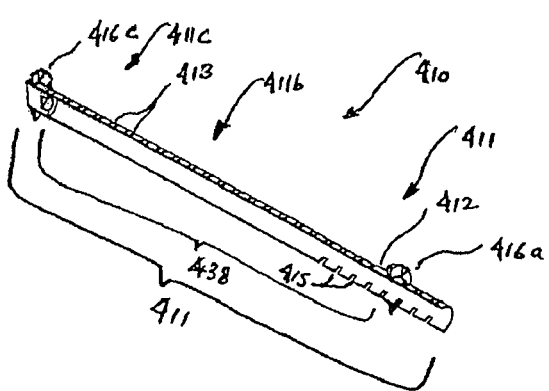
FIG. 15 is a perspective cross-sectional view of the anastomotic view of FIG. 14 following deployment.
Figure 16:
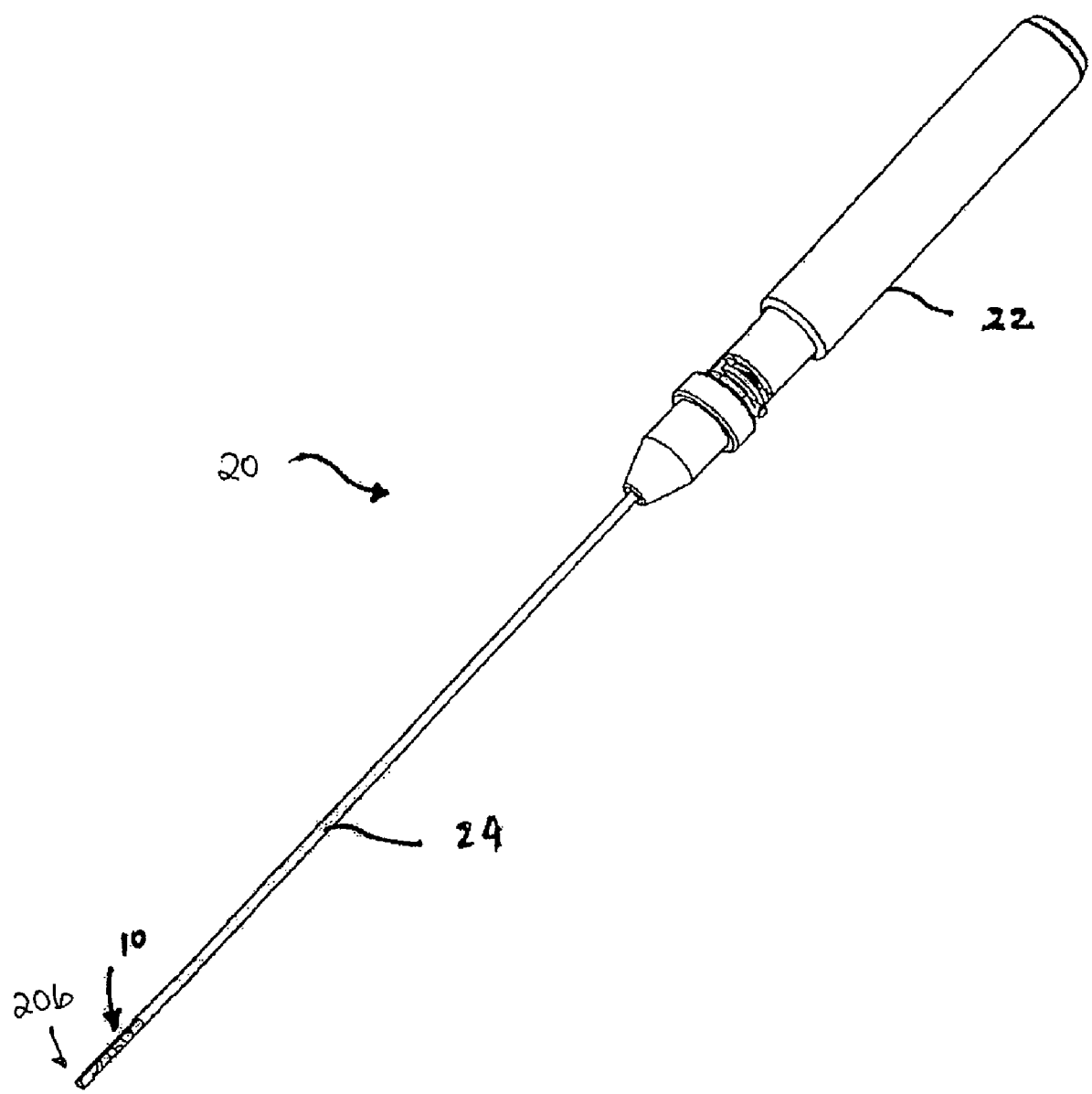
FIG. 16 is a perspective view of one exemplary embodiment of an actuator for deploying an anastomotic device, showing an anastomotic device coupled thereto.
Figure 19:
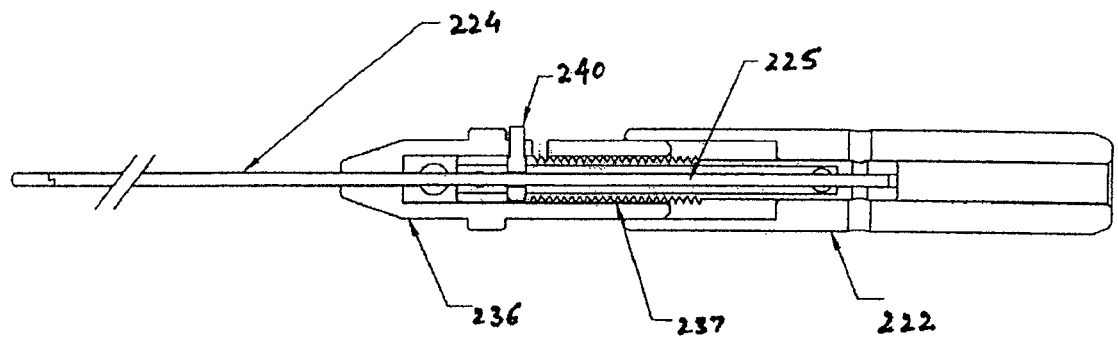
FIG. 19 is a cross-sectional view of the handle portion of the actuator of FIG. 16.

Another exemplary embodiment of an anastomotic device 410 is illustrated in FIGS. 11-15. The device 410 is configured to have an adjustable length. As shown, the device 410 is in the form of two separate elongated tubular bodies 411, 412 that couple together to form a connector 438 therebetween. The connector 438 can be adjusted, for example, to match a thickness of tissue wall. In one embodiment, a diameter of tubular body 411 is smaller than a diameter of tubular body 412 and a length of tubular body 411 is longer than tubular body 412. As illustrated in the un-deployed device 410 of FIG. 11, tubular body 411 has a distal portion 411c configured to radially expand, an intermediate portion 411b, and a proximal portion 411a configured to allow a longitudinal position of tubular body 412 to be adjusted relative to tubular body 411. The distal portion 411c can include a plurality of slits 414c formed therein and configured to allow portions of the elongate tubular body 411 between the plurality of slits 414c to radially expand. In the illustrated embodiment the slits 414c are substantially S-shaped to expand in a radial direction and form wings 416c, as shown in FIGS. 14 and 15. The intermediate portion 411b can be flexible. In the illustrated embodiment, slits 413 are formed therein to provide desired flexibility. The slits can be in a variety of patterns and can be formed in a variety of manners, for example, by laser-cutting. As shown in FIG. 12, the proximal portion 411a can include a plurality of slots 415 formed therein and configured to position the tubular body 412 with respect to the proximal portion 411a. The slots 415 can be any shape and size, including curved, and can be formed using a variety of manners, for example by laser-cutting.

Tubular body 412 can be configured to slide over at least a portion of the proximal portion 411a of tubular body 411. Tubular body 412 has a distal portion 412c configured to engage the slots 415 of the proximal portion 411a of tubular body 411 and a proximal portion 412a configured to radially expand. The proximal portion 412a can include a plurality of slits 414a formed therein and configured to allow portions of the elongate tubular body 412 between the plurality of slits 414a to radially expand. In the illustrated embodiments the slits 414a are substantially S-shaped to expand in a radial direction and form wings 416a, as shown in FIGS. 14 and 15. The distal portion 412b can include one or more flaps 419 configured to engage the slots 415 of the tubular body 411. In the illustrated embodiment of FIG. 13, the flaps 419 are bent in an inward direction toward the slots 415 such that the tubular body 412 can move toward the tubular body 411 and can lock in place when moved away from the tubular body 411. A person having ordinary skill in the art would recognize that a variety of other configurations can be used to allow tubular body 412 to be fixed in various positions along the proximal portion 411a of tubular body 411, including embodiments in which tubular body 412 can be moved in either direction with respect to tubular body 411. In one embodiment, the proximal portion 412a of tubular body 412 includes tabs 423 to assist with the introduction of the tubular bodies 411, 412 to the anastomosis. A person having ordinary skill in the art would recognize that in other embodiments tabs 423 can be formed in tubular body 411 in a similar manner for a similar purpose. FIGS. 14 and 15 illustrates the device 410 in its final form. In particular, the wings 416c, 416a of the tubular bodies 411, 412 have been deployed and the connector 438 adjusted to a desired length by setting a position of tubular body 412 with respect to the proximal portion 411a of tubular body 411. Although bodies 411, 412 are discussed as being tubular, a person having ordinary skill in the art would recognize that other shapes can also be used to form the bodies 411, 412.

Similar to the tubular body 12, each of the tubular bodies 311, 312, 411, and 412 can be formed from a variety of materials including absorbable and non-absorbable materials. In an exemplary embodiment, the devices 310, 410 are formed from a deformable material that undergoes plastic deformation (i.e., deformation with negligible elastic component). Exemplary materials include, by way of non-limiting example, any resorbable (e.g., biocompatible and/or bioabsorbable) materials, including, for example, titanium (and titanium alloys), magnesium alloys, stainless steel, polymeric materials (synthetic and/or natural), shape memory material such as nitinol, ceramic, etc. Materials which are not normally radiopaque, e.g., magnesium alloy, may be enhanced and made x-ray visible with the addition of x-ray visible materials, such as particles of iron oxide, stainless steel, titanium, tantalum, platinum, or any other suitable equivalents. Further, the materials discussed below with respect to the shunts can also be used to form and/or coat the tubular body 311, 312, 411, and 412, including non-permeable materials, such as polyethylene terephthalate and polyvinylidene chloride, and semi-permeable materials, such as polylactide.

While various techniques can be used to deploy and actuate the devices 10, 310, and 410, such as techniques disclosed in the '131 Application, in one exemplary embodiment an anastomotic device 10''', which is of a similar nature as anastomotic device 10, is removably coupled to an actuator that can be adapted to guide the device 10''' into a body lumen and to apply an axial and rotational force to an elongate tubular body 12''' to cause the elongate tubular body 12''' to extend outwardly. FIGS. 16-25 illustrate one exemplary embodiment of an actuator 200 for deploying the anastomotic device 10'''. In general, the actuator 200 includes a proximal portion in the form of a handle 222 and an elongate shaft extending distally from the handle. A distal end of the actuator 200 includes a digital gripper assembly 228 that is adapted to removably couple to the anastomotic device 10'''. The elongate shaft includes an outer shaft or former 224 that is disposed around and coupled to an assembly shaft 225, which itself is disposed around an inner shaft 226. The inner shaft 226 is effective to hold a portion of the device 10''' in a fixed position by expanding the assembly shaft 225 (and possibly also the former 224) to allow the digital gripper assembly 228, which is formed on the distal end of the assembly shaft 225, to engage the device 10''', as described further below. With both the inner and assembly shafts 226, 225 disposed within the former 224, the former 224 can be effective to apply axial and/or rotational forces to the anastomotic device 10''' to deploy the anastomotic device 10'''.

The former 224 can have a variety of configurations, but it is preferably adapted to detachedly couple to a proximal end 10a''' of the anastomotic device 10'''. While various techniques can be used to couple the former 224 to the anastomotic device 10, FIGS. 17 and 18 illustrate one exemplary technique. As shown, the former 224 includes one or more protrusions 224a that can extend into one or more notches formed between tabs 15a''' formed in the proximal end 10a''' of the device 10''' such that the protrusions 224a and tabs 15a''' interlock. Similarly, the digital gripper assembly 228 can also have a variety of configurations, but it is shown as an expandable tubular member having one or more protrusions 228b that can extend proximally into one or more notches formed between tabs 15a''' formed in the proximal end 10a''' of the device 10''' such that the protrusions 228b and tabs 15a''' interlock. The distal gripper assembly 228 can be attached to or formed on the distal end of the assembly shaft 225, which is slidably disposed through the former 224. For example, the distal gripper assembly 228 can be attached to the anastomotic device 10''' using a threaded attachment. Furthermore, the distal gripper assembly 228 can include one or more thinned or weakened regions to help it collapse for its detachment and removal from the outer elongate body 12 as described further below. The thinned or weakened region(s) can be achieved by reducing the amount of material at that region, or by scoring or otherwise removing some of the material used to form the distal gripper assembly 228.

The former 224 and/or the assembly shaft 225 can also be configured to provide maximum flexibility during clinical use, while the inner shaft 226 can be rigidly configured to provide structural support to the former 224 and/or the assembly shaft 225. For example, the former 224 and/or the assembly shaft 225 can be formed from a flexible material, or the former 224 and/or the assembly shaft 225 can include one or more flexible regions formed thereon.

In order to rotate the former 224 relative to the assembly shaft 225 and the inner shaft 226 and thereby form wings 16a''', 16b''', the handle 222 of the actuator 220 can optionally include an actuation mechanism formed thereon. In an exemplary embodiment shown in FIGS. 19-22, the handle 222 includes an outer collar 236 that can be coupled to a proximal portion of the former 224 such that rotation of the collar 236 is effective to rotate the former 224. The proximal end of the assembly shaft 225 can also include an inner collar 237 that is attached to the assembly shaft 225 and that includes a pin 240 formed thereon or extending therefrom. The pin 240 extends through and is positioned within the guide tracks 238. Since the position of the pin 240 is fixed due to the assembly shaft 225 being fixed, movement of the outer collar 236, and thus the former 224, is governed by the configuration of the guide tracks 238 which can move relative to the fixed pin 240. As a result, the guide tracks 238 can be used to control the axial and rotational forces applied to the anastomotic device 10''' coupled to the distal end of the former 224.

Figure 20:
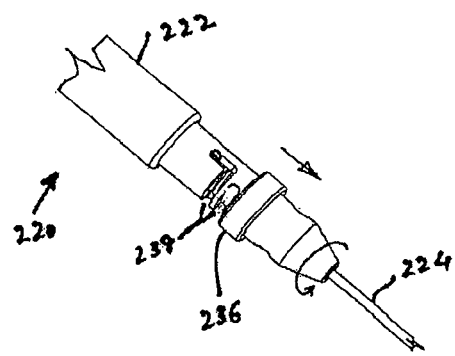
FIG. 20 is a perspective view of a proximal portion of the actuator of FIG. 19 in an initial, starting position.
Figure 21:
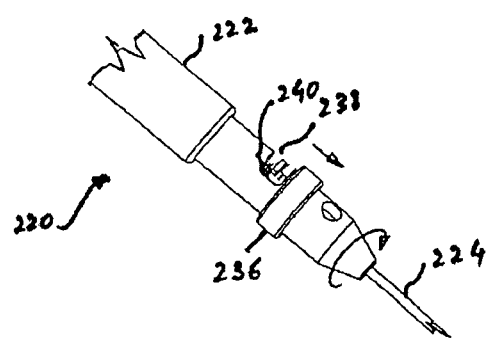
FIG. 21 is a perspective view of the proximal portion of the actuator shown in FIG. 20 following deployment of the distal wings of an anastomotic device.
Figure 22:
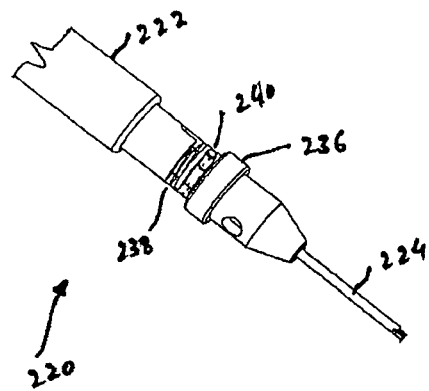
FIG. 22 is a perspective view of the proximal portion of the actuator shown in FIG. 21 following deployment of the proximal wings of the anastomotic device.

As shown in FIGS. 20-22, the guide tracks 238 can have a configuration that allows the collar 236 to rotate in a first direction, e.g., counter clockwise, to deploy the distal wings 16b''' of the anastomotic device. The distal wings 16a''', 16b''' can be deployed before or after the proximal wings 16a''', although they are deployed first in this example. In particular, as the outer collar 236 is rotated counter clockwise, the former tube 224 will rotate in a counter-clockwise direction, thereby rotating the proximal end 10a''' of the anastomotic device 10''' to expand the distal wings 16b''' of the anastomotic device 10'''. The gripper 228 will remain in a fixed position, thus holding the distal end 10b''' of the device 10''' in a fixed position while the proximal end 10a''' is rotated. As previously discussed, since slits 14a''', 14b''' in distal and proximal portions 12a''', 12b''' preferably extend in opposite directions, rotation of the anastomotic device 10''' in a first direction will only deploy the distal wings 16b'''. Once the outer collar 236 is fully rotated, the guide tracks 238 can allow distal movement of the outer collar 236, while the guide pin 240 remains in a fixed position at all times, thus allowing the outer collar 236 to be advanced distally. As a result, the former tube 224 will apply compressive forces on the anastomotic device 10''', thereby causing the distal wings 16b''' to collapse into a substantially planer configuration.

The guide tracks 238 can then allow the outer collar 236 to rotate in an opposite direction, e.g., a clockwise direction, to cause the former tube 224 to rotate clockwise. As the former 224 rotates clockwise, the proximal wings 16a''' will expand. Once the outer collar 236 is fully rotated, the guide tracks 238 can allow distal movement of the outer collar 236 therein, thus allowing the outer collar 236 to be advanced distally. As a result, the former tube 224 will apply compressive forces on the anastomotic device 10''', thereby causing the proximal wings 16a''' to collapse into a substantially planar configuration in which they extend transverse to the axis A (see FIG. 1) of the device 10'''.

A person skilled in the art will appreciate that the guide tracks 238 can have a variety of other configurations. For example, rather than allowing rotation, and then distal movement, the guide tracks 238 can extend at an angle around the handle 222 to allow rotational and compressive forces to be simultaneously applied to the anastomotic device 10'''. A person skilled in the art will appreciate that a variety of other techniques can be used to actuate the former 224 to deploy the device.

Once the device 10''' is deployed, the actuator 200 can be removed. For example, the distal gripper assembly 228 can be configured such that it can disengage from the outer elongate body 12''' when a force is applied thereto. In use, the distal gripper assembly 228 can be collapsed by removing the inner shaft 226, which allows the distal gripper assembly 228 to return to an unexpanded state in which it can be retracted through the device 10'''. During use, the distal gripper assembly 228 can be rotated relative to the anastomotic device 10''' so as to unscrew the distal gripper assembly 228 from the anastomotic device 10'''. Once detached, the distal gripper assembly 228 (and former 224) can be removed from the patient, leaving the anastomotic device 10''' in position at the anastomotic site. A person skill in the art will appreciate that a variety of mating techniques can be used, including, for example, an interference fit, a mechanical interlock, etc.

Figure 23:
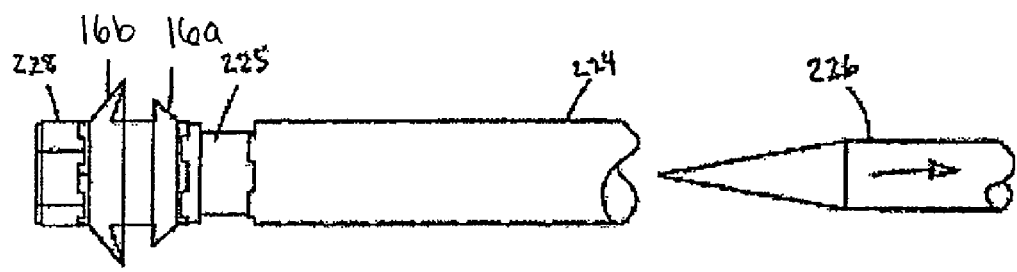
FIG. 23 is a side view of the anastomotic device of FIG. 16 and an inner shaft of the actuator of FIG. 16 being removed from the anastomotic device.
Figure 24:
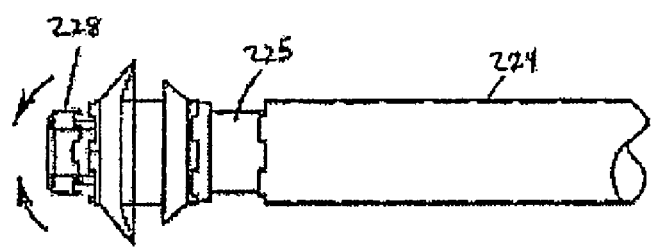
FIG. 24 is a side view of the anastomotic device of FIG. 23 and a distal gripper assembly of the actuator being removed from the anastomotic device.
Figure 25:
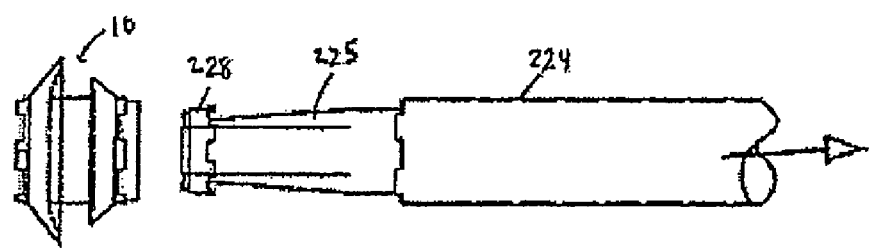
FIG. 25 is a side view of the anastomotic device of FIG. 24 and the remainder of the actuator being removed from the anastomotic device.
Figure 26:
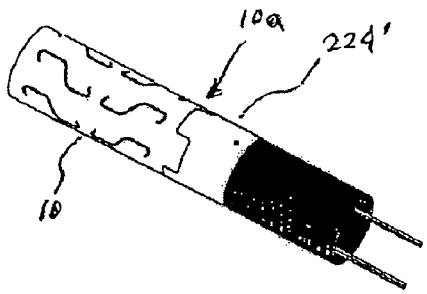
FIG. 26 is a perspective view of one exemplary embodiment of a former of an actuator for deploying an anastomotic device, showing the anastomotic device of FIG. 16 coupled thereto in an initial, unformed configuration.
Figure 27:
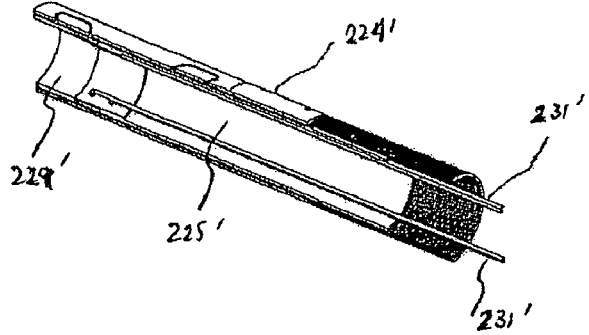
FIG. 27 is a cross-sectional perspective view of the anastomotic device and the inner shaft of FIG. 26.

FIGS. 23-25 illustrate a distal portion of the outer shaft 224, the assembly shaft 225, and the inner shaft 226 of the actuator 200 in use with the anastomotic device 10'''. Following deployment of the anastomotic device 10''', the actuator 200 is preferably disconnected and removed from the patient. In FIG. 23, the protrusions 224a on the former 224 are removed from the corresponding cut-outs formed between the tabs 15a''' in the proximal end 10a''' of the device 10'''. The inner shaft 226 can then be withdrawn from the assembly shaft 225 and the outer shaft 224 in a distal direction. Removing the inner shaft 226 can cause the distal end of the assembly shaft 225 to collapse inwards as shown by the directional arrows in FIG. 24. The diameter of the assembly shaft 225 can thereby be reduced so that it and the attached or coupled distal gripper assembly 228 can be moved through the anastomotic device 10'''. The entire remaining actuator assembly (e.g., the assembly and outer shafts 225, 224) can be withdrawn in a distal direction as shown in FIG. 25, thereby leaving the device 10''' deployed and engaging tissue. The device 10''' can also be removed from the body after deployment, if necessary. For example, the wings 16a''', 16b''' can be collapsed to their original, flat, undeployed configuration and the device 10''' can be removed from the body.

Figure 28:
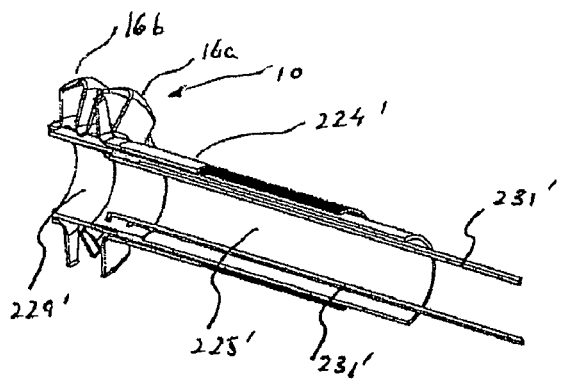
FIG. 28 is a cross-sectional perspective view of the anastomotic device and the inner shaft of FIG. 27 following deployment.
Figure 29:
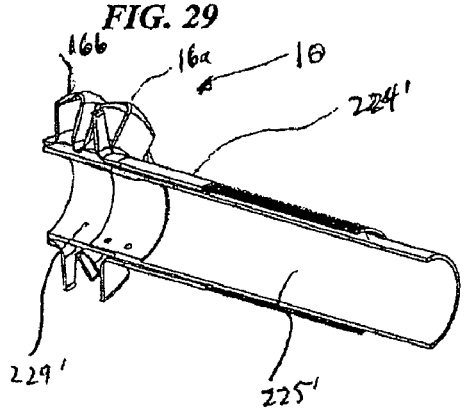
FIG. 29 is a cross-sectional perspective view of the anastomotic device and the inner shaft of FIG. 28 following deployment with sutures removed.
Figure 30:
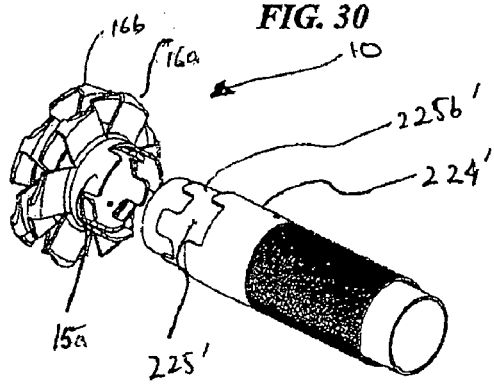
FIG. 30 is a perspective view of the anastomotic device following deployment with the former and inner shaft de-coupled therefrom.
Figure 31:
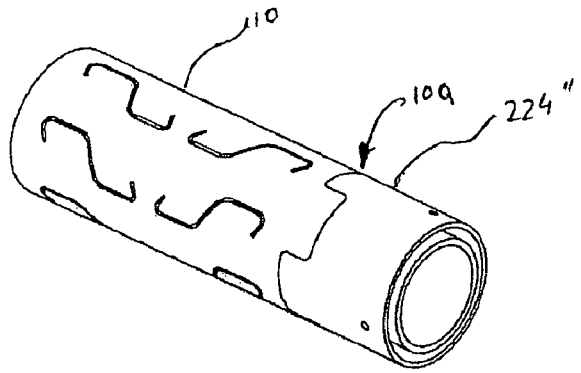
FIG. 31 is a perspective view of another exemplary embodiment of a former of an actuator for deploying an anastomotic device, showing the anastomotic device of FIG. 1 coupled thereto in an initial, unformed configuration.
Figure 32:
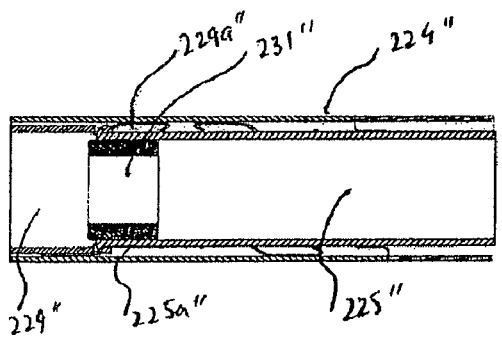
FIG. 32 is a cross-sectional side view of the anastomotic device and an inner shaft of the former of FIG. 31.

FIGS. 26-30 illustrate another technique that can be used to deploy and actuate the devices 10, 310, and 410. For example, anastomotic device 10 can be removably coupled to an actuator that is similar to actuator 200. The actuator can include an elongate shaft extending from a handle and the elongate shaft can include an outer shaft or former 224'. Former 224' has a configuration that is similar to the configuration of former 224 except that the digital gripper assembly 228 is replaced by an elongated tubular body 229'. Former 224' can be effective to apply axial and/or rotational forces to the anastomotic device 10 to deploy the anastomotic device 10. A distal end of the elongated tubular body 229' can be coupled to a proximal end 10a of the device 10 in a variety of ways, some of which are discussed above with respect to the gripper assembly 228. Similarly, the elongated tubular body 229' can also have a variety of configurations. As shown, an inner tube 225' can be disposed in the elongated tubular body 229'. The inner tube 225' can include one or more notches formed between tabs 230' formed in a distal end 225b' of the inner tube 225' such that the notches and the tabs 15a formed in the proximal end 10a of the anastomotic device 10 can interlock. The inner tube 225' can be coupled to the elongated tubular body 229' in a variety of ways, but in one exemplary embodiment illustrated best in FIGS. 27 and 28, it is connected axially with the tubular body 229' using one or more sutures 231'. The sutures 231' can be at least partially disposed in the tube 225' and the free ends can be attached to an actuator. The sutures 231' can be configured to hold the anastomotic device 10 to the former 224' and the inner tube 225'. Although portions of the anastomotic device 10 can be configured to rotate, in use the sutures 231' can be configured such that they generally do not rotate because of the notches and tabs coupling the device 10, former 224', and inner tubes 225'. The sutures 231' can be configured to experience tensile forces though, for example, when the former 224' applies compressive forces. FIG. 28 illustrates one instance in which the wings 16a, 16b of the anastomotic device 10 have been deployed and the former 224', inner shaft 225', and sutures 231' each remain intact. As shown in FIG. 29, the sutures 231' can be removed, for example by manually removing them from the outside or by using a mechanism for suture removal incorporated with the actuator. As shown in FIG. 30, the anastomotic device 10 can be de-coupled from the former 224' and inner tube 225' using a variety of different methods, including those discussed with respect to the former 224.

Figure 33:
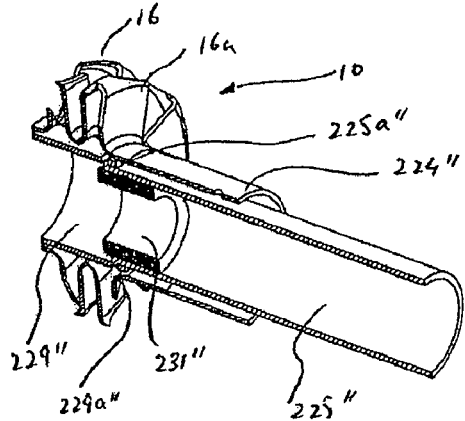
FIG. 33 is a cross-sectional perspective view of the anastomotic device and the inner shaft of FIG. 31 following deployment.
Figure 34:
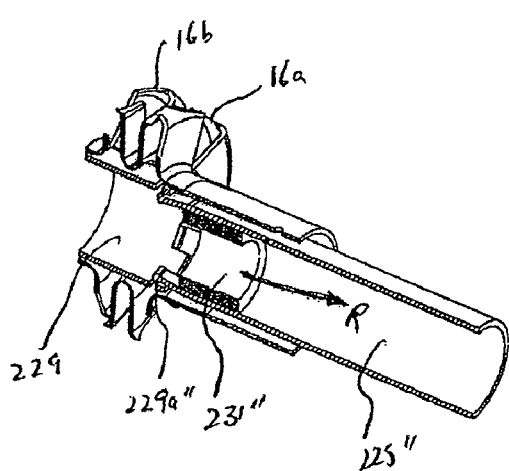
FIG. 34 is a cross-sectional perspective view of the anastomotic device and the inner shaft of FIG. 33 following deployment with the former and the inner shaft being removed.
Figure 35:
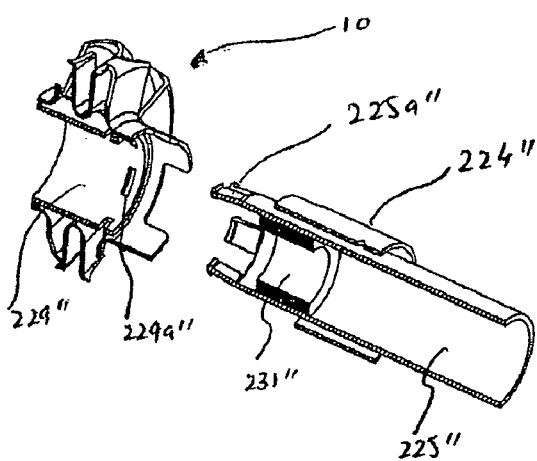
FIG. 35 is a cross-sectional perspective view of the anastomotic device and the inner shaft of FIG. 34 following deployment with the former and the inner shaft de-coupled therefrom.

FIGS. 31-35 another technique that can be used to deploy and actuate the devices 10, 310, and 410. For example, anastomotic device 10 can be removably coupled to an actuator that is similar to actuator 200. The actuator can include an elongate shaft extending from a handle and the elongate shaft can include an outer shaft or former 224". Former 224" has a configuration that is similar to the configuration of former 224 except that the digital gripper assembly 228 is replaced by an elongated tubular body 229". Former 224" can be effective to apply axial and/or rotational forces to the anastomotic device 10 to deploy the anastomotic device 10. A distal end of the elongated tubular body 229" can be coupled to a proximal end 10a of the device 10 in a variety of ways, some of which are discussed above with respect to the gripper assembly 228. Similarly, the elongated tubular body 229" can also have a variety of configurations. As shown, an inner tube 225" can be disposed in the elongated tubular body 229". In one embodiment the elongated tubular body 229" and the inner tube 225" can include features that allow them to couple together to hold the inner tube 225" in a desired location. For example, the inner tube 225" can include one or more protrusions 225a" configured to engage with one or more slots 229a" of the elongated tubular body 229" to hold the inner tube 225" in a variety of locations. In a first position of the inner tube 225", the protrusions 225a" can have a small cone angle and they can be disposed within the slots 229a" by pushing a tubular body 231" disposed within the tubular body 229", thereby locking the tubular body 229" in a desired location. Accordingly, as illustrated in FIG. 33, as the anastomotic device 10 is deployed, the former 224", the inner tube 225", and the elongated tubular body 229" can remain intact while the wings 16a, 16b of the device 10 are deployed. The protrusions 225a" can also be disengaged from the slots 229a", as illustrated in FIG. 34, by pulling in a direction R on the elongate tubular body 229". A shown in FIG. 35, the anastomotic device 10 can be de-coupled from the former 224", the inner tube 225", and the tubular body 229" using a variety of different methods, including those discussed with respect to the former 224.

Figure 36:
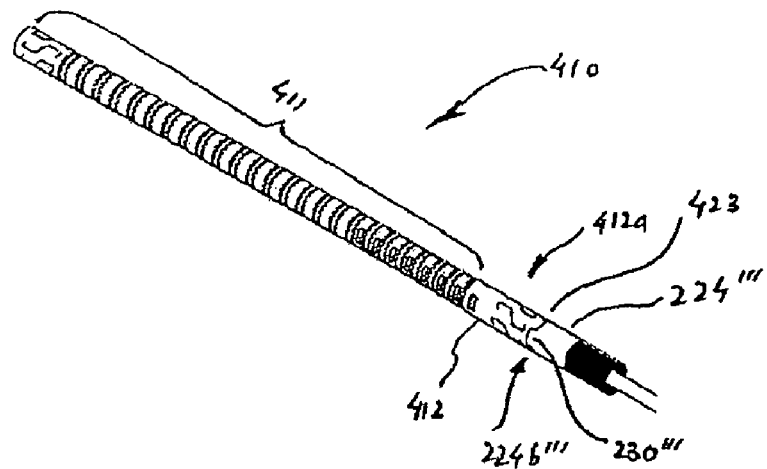
FIG. 36 is a perspective view of another exemplary embodiment of a former of an actuator for deploying an anastomotic device, showing the anastomotic device of FIG. 11 coupled thereto in an initial, unformed configuration.
Figure 37:
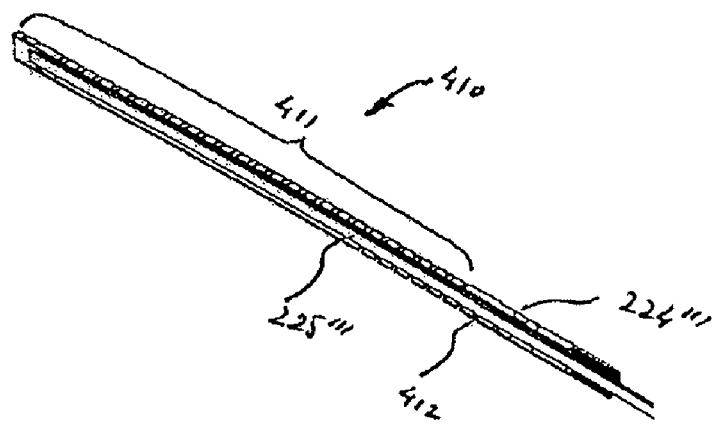
FIG. 37 is a cross-sectional perspective view of the anastomotic device and an inner shaft of the former of FIG. 36.
Figure 38:
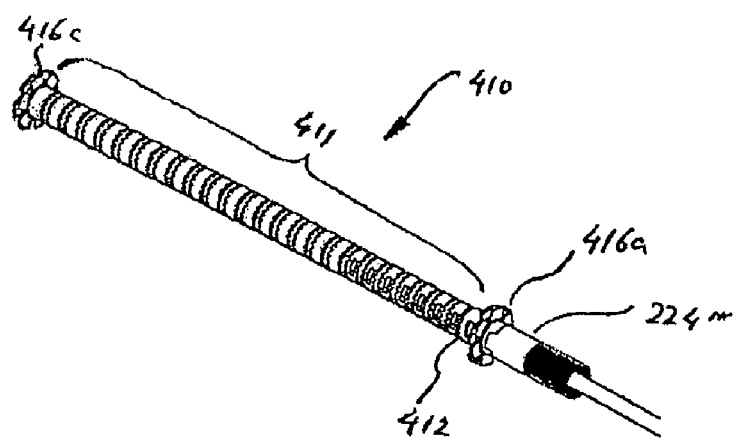
FIG. 38 is a perspective view of the anastomotic device of FIG. 37 following deployment.
Figure 39:
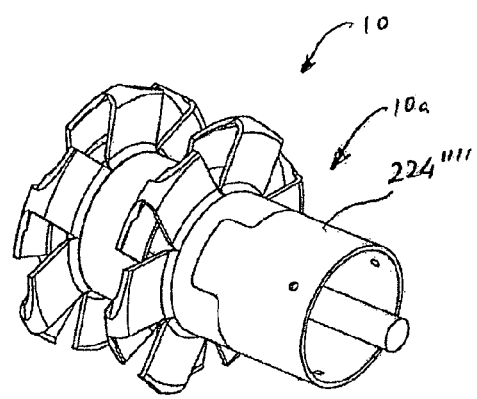
FIG. 39 is a perspective view of another exemplary embodiment of a former of an actuator for deploying an anastomotic device, having a forced release mechanism disposed therein, showing the anastomotic device of FIG. 1 coupled to both the former and the forced release mechanism and in a deployed configuration.

FIGS. 36-38 illustrate yet another technique that can be used to deploy and actuate the devices 10, 310, and 410. For example, anastomotic device 410 can be removably coupled to an actuator that is similar to actuator 200. The actuator can include an elongate shaft extending from a handle and the elongate shaft can include an outer shaft or former 224'''. Former 224''' has a configuration that is similar to the configuration of former 224 and it can be effective to apply axial and/or rotational forces to the anastomotic device 410 to deploy the anastomotic device 410. A distal end 224b''' of the former 224''' can be coupled to a proximal end 412a of the tubular body 412 of the device 410 in a variety of ways, some of which are discussed above with respect to former 224. As shown, the distal end 224b''' of the former 224''' can include one or more notches formed between tabs 230''' such that the notches and the tabs 423 formed in the proximal end 412a of the tubular body 412 of the anastomotic device 410 can inter-lock. As shown in FIG. 37, an inner tube 225''' can be disposed in the actuator and the tubular body 411 can be attached thereto while the former 224''' can be coupled with the proximal end 412a of the tubular body 412. The anastomotic device 410 can be deployed while the former 224''' and the inner tube 225''' are still coupled to the tubular body 412, as shown in FIG. 38.

Figure 40:
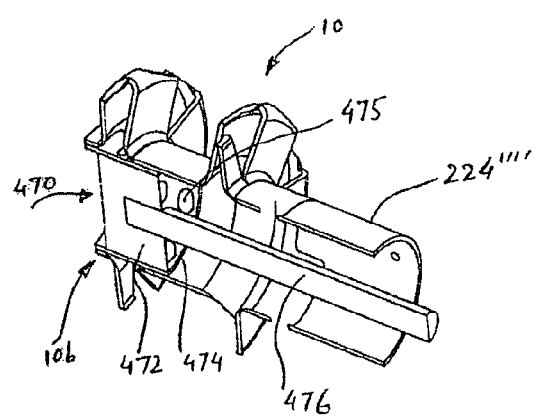
FIG. 40 is a cross-sectional perspective view of the anastomotic device, the former, and the forced release mechanism of FIG. 39.
Figure 41:
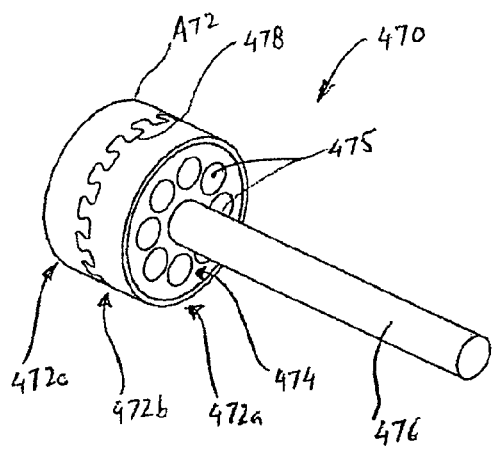
FIG. 41 is a perspective view of the forced release mechanism of FIG. 40
Figure 42:
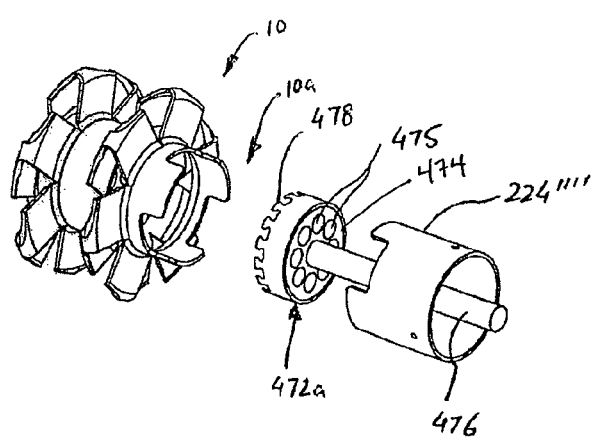
FIG. 42 is a perspective view of the anastomotic device, the former, and the forced release mechanism of FIG. 40 with the former and the forced release mechanism de-coupled from the anastomotic device.

FIGS. 39-42 illustrate still another technique that can be used to deploy and actuate the devices 10, 310, and 410, which uses a force release mechanism 470. For example, anastomotic device 10 can be removably coupled to an actuator that is similar to actuator 200. The actuator can include an elongate shaft extending from a handle and the elongate shaft can include an outer shaft or former 224''''. Former 224'''' has a configuration that is similar to the configuration of former 224 except that the digital gripper assembly is replaced by a forced ejection mechanism 470, which is disposed through former 224'''' and coupled to the anastomotic device 10. Former 224'''' can be effective to apply axial and/or rotational forces to the anastomotic device 10 to deploy the anastomotic device 10. A distal end of former 224'''' can be coupled to a proximal end 10a of the device in a variety of ways, some of which are discussed above with respect to the gripper assembly 228. As illustrated by FIGS. 40 and 41, the forced ejection mechanism 470 can include a tubular body 472 that is configured to couple to the distal end 10b of the anastomotic device 10. In one embodiment a distal end 472c of the tubular body 472 is welded to the distal end 10b of the anastomotic device 10. Further, a proximal end 472a of the tubular body 472 can be coupled to a proximal end of a body portion 474, for example by welding. As shown the body portion 474 is cylindrical, although other shapes that generally fit well with the shape of the anastomotic device can be used. In the illustrated embodiment, the body portion 474 includes one or more perforations 475 that can allow a contrast medium to pass therethrough. In other embodiments the body portion 474 can be solid. An elongate member 476 can be coupled to the body portion 474. In the illustrated embodiment, a center portion of the body portion 474 includes a hole that is configured to receive the elongate member 476 and the elongate member 476 is fit into the hole, for example by welding or press-fitting the elongate member 476 within the hole. In one embodiment the elongate member 476 is hollow to allow fluid, such as contrast medium, to pass through or to allow a guidewire to pass therethrough such that the elongate member 476 can slide along the guidewire. The elongate member 476 can be made of a variety of materials, including nitinol, stainless steel, titanium, or a variety of bio-compatible materials. A mid-portion 472b of the tubular body 472 can include a breaking boundary 478 that is configured to allow the proximal end 472a to separate from the distal end 472c of the tubular body 472. This can occur before or while the former 224'''' is being separated from the anastomotic device 10. In one exemplary embodiment the breaking boundary 478 is patterned by a laser cut. The shape of the breaking boundary 478 can be any number of shapes that are configured to apply rotational force and withstand a specified axial force. The breaking boundary 478 can break when the axial force exceeds the specified limit. Specifically, the size, shape, and design of the breaking boundary can be altered to achieve a desired breaking force. As shown in FIG. 42, a breaking force can be applied to the tubular body 472, which can decouple the anastomotic device 10 from the former 224'''' such that the proximal end 472a of the tubular body 472 and the former 224'''' can be removed from a placement site, thereby leaving the deployed anastomotic device 10 and a distal end 472c of the tubular body 472 at the placement site. The distal end 472c of the tubular body 472 can be configured to allow fluid to pass therethrough, or alternatively, it can be removed. Further, although the tubular body 472 is discussed as being tubular, a person having ordinary skill in the art would recognize that other shapes can also be used for the body 472.

As indicated above, the methods disclosed herein for forming a bypass can also include forming a surrogate pathway between a patient's esophagus and an anastomosis formed between the patient's stomach and intestine. The surrogate path allows fluid to at least partially be directed from the esophagus to the intestine through a connection formed between a patient's stomach and a portion of a patient's intestine. The surrogate path can be formed using any device or combination of devices that is configured to redirect fluid, generally referred to herein as a shunt. Some examples of shunts that can be used to form a surrogate path include a simple tube, catheter, stent, or any elongate member. The shunt is generally configured to form a surrogate path to bypass at least a portion of a patient's stomach, up to the entire stomach. In one exemplary embodiment, the shunt extends between a patient's esophagus and an anastomosis formed between the patient's stomach and the intestine (i.e., a gastro-entero anastomosis) to bypass a patient's stomach completely. The shunt can include a proximal end configured to receive fluid from the esophagus and a distal end configured to direct fluid to a patient's intestine. The shunt can be configured to couple with or pass through an anastomotic device, or alternatively, it can be integrally formed with an anastomotic device. A variety of anastomotic devices, including the devices 10, 310, and 410, can be configured to couple with the shunt or be integrally formed with the shunt. Optionally, the shunt can include a one-way valve configured to inhibit acid reflux. While capable of inhibiting acid reflux, the one-way valve is also preferably configured to allow the flow of fluid back through the shunt if induced by an action such as regurgitation. One way of configuring the one-way valve to resist fluid from flowing back up the shunt because of acid reflux but allowing fluid from flowing back up the shunt because of regurgitation is by setting a threshold pressure of the one-way valve to resist opening based on pressure exerted on the valve typical of acid reflux and opening based on the pressure exerted on the valve typical of regurgitation. The shunt can optionally be porous to allow some fluid to dissipate through the shunt and into the stomach, but preferably the shunt is non-porous.

Figure 43:
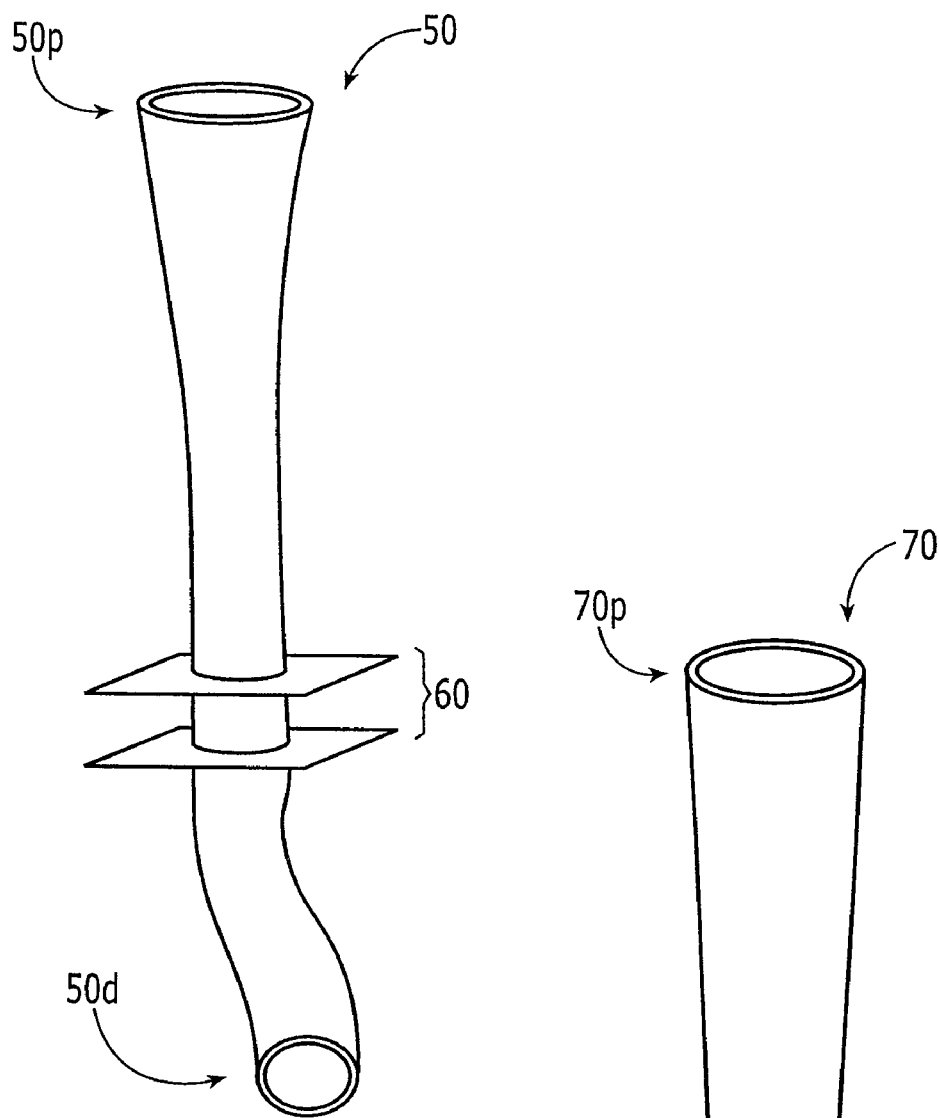
FIG. 43 is a side view of one exemplary embodiment of a shunt having an anastomotic device integrally formed thereon.

One exemplary embodiment of a shunt is illustrated in FIG. 43. The shunt is a linear-shaped shunt 50 that includes a proximal end 50p configured to receive fluid and a distal end 50d configured to direct fluid in a single direction. As illustrated, the linear-shaped shunt 50 is integrally formed with an anastomotic device 60 to form a combination shunt and anastomotic device, although in alternative embodiments the shunt and anastomotic device can be separate. The linear-shaped shunt 50 is configured to extend from an esophagus, through a stomach, and into an intestine of a patient via a gastro-entero anastomosis. In other embodiments, for instance where the shunt is not configured to extend all the way between the esophagus and the intestine, the shunt can include a separate tube configured to couple to the proximal or distal end of the shunt. In use, the distal end 50d of the linear-shaped shunt 50 can be configured to direct fluid in a single direction. For example, it can direct fluid through the anastomosis toward a distal portion of the intestine, as will be discussed in more detail below.

Figure 44:
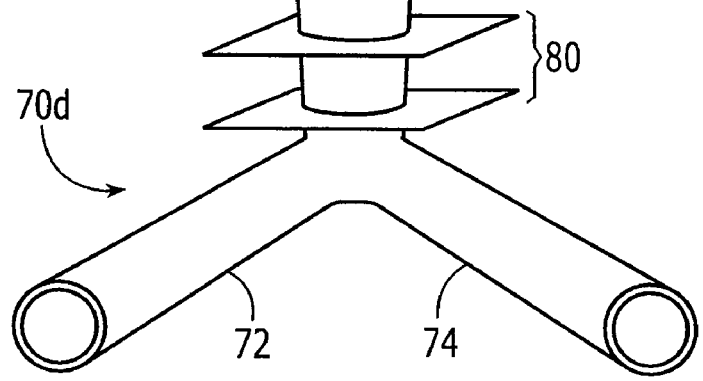
FIG. 44 is a side view of another exemplary embodiment of a shunt having an anastomotic device integrally formed thereon.

In another exemplary embodiment, illustrated in FIG. 44, the shunt can be a Y-shaped shunt 70 that includes a proximal end 70p configured to receive fluid and a distal end 70d configured to direct fluid in two directions. As illustrated, the Y-shaped shunt 70 is integrally formed with an anastomotic device 80 to form a combination shunt and anastomotic device, although in alternative embodiments the shunt and anastomotic device can be separate. In particular, the distal end 70d of the shunt 70 is Y-shaped to allow a first leg 72 to extend in a first direction, i.e., toward a proximal portion of the intestine, and to allow a second leg 74 to extend in a second opposite direction, i.e., toward a distal portion of the intestine. Allowing fluid flow in both directions can be advantageous because it allows more vitamins, minerals, and nutrients to be absorbed by the intestine since the proximal portion of the intestine is not completely bypassed.

The shunt can be formed from a variety of materials depending on the desired capabilities of the shunt. For example, the shunt can be formed of a non-permeable polymer, such as polyethylene terephthalate, so that fluid that flows therethrough does not penetrate through the device and into the stomach. Non-permeability can also be achieved by way of a non-permeable coating, such as polyvinylidene chloride. Alternatively, it can be desirable to allow some fluid to dissipate into the body, in which case a semi-permeable polymer, such as polylactide, can be used to form the shunt or to form a coating for the shunt. Forming the shunt from a semi-permeable polymer can allow vitamins, minerals, and nutrients found in fluid to dissipate into the stomach. Other materials, such as those suitable for forming an anastomotic device as discussed above, can also be used to form a shunt. Similarly, materials which are not normally radiopaque, e.g., magnesium alloy, may be enhanced and made x-ray visible with the addition of x-ray visible materials, such as particles of iron oxide, stainless steel, titanium, tantalum, platinum, or any other suitable equivalents. It can also be desirable to configure the shunt such that it can expand. Materials can be selected to form the shunt that have expandable properties, such as elastomeric polymers. In some embodiments the shunt can be designed to be self-expanding, balloon-expandable, rigid-covered, or open-framed.

In an exemplary embodiment, a method for treating obesity generally entails forming a fluid connection between a stomach and an intestine and forming a surrogate path from an esophagus to the intestine so fluid is at least partially directed from the esophagus to the intestine through the connection, thereby at least partially bypassing the stomach. The method can also include forming a connection between two portions of the intestine—one portion distal to the fluid connection between the stomach and the intestine and one portion proximal to the fluid connection between the stomach and the intestine—to form a single intestine loop. The connections between the stomach and the intestine and the two portions of the intestine can be formed in any order. The surrogate path can extend to one or both of the proximal and distal portions of the intestine. At either or both of the connections, an anastomotic device can be disposed therein, such as the device 10 previously described herein. Further, the surrogate path can be formed by inserting a shunt through the anastomotic device at the connection between the stomach and the intestine, or alternatively, the surrogate path can be formed by implanting an anastomotic device having a shunt integrally formed thereon. Either or both of the anastomotic device and the shunt can be delivered to desired locations using a variety of techniques, including, by way of non-limiting examples, those discussed herein and those discussed in the '131 Application.

In one exemplary embodiment for treating obesity, illustrated in FIGS. 45A-45F, a gastric bypass procedure is performed that includes forming a connection (i.e., an entero-entero anastomosis 110) between two portions 150a, 150c of an intestine 150 prior to forming a connection (i.e., a gastro-entero anastomosis 120) between a stomach 140 and a portion of the intestine 150 located between the two portions 150a, 150c. In an exemplary embodiment the procedure can begin by inserting an endoscope in the body using a natural body orifice in accordance with NOTES procedures. Using natural body orifices to perform the procedure is generally preferred because it obviates the need for any additional incisions in the abdominal wall, intestine, or in any other part of the body beyond those needed to form anastomoses. Nevertheless, laparoscopic methods can also or alternatively be used. If using a laparoscopic method, a trocar assembly can be inserted into the surgical site, e.g., the stomach, at any number of locations in the stomach, including the epigastrium, the flank, and the mesogastrium.

Figures 45A, 45B:
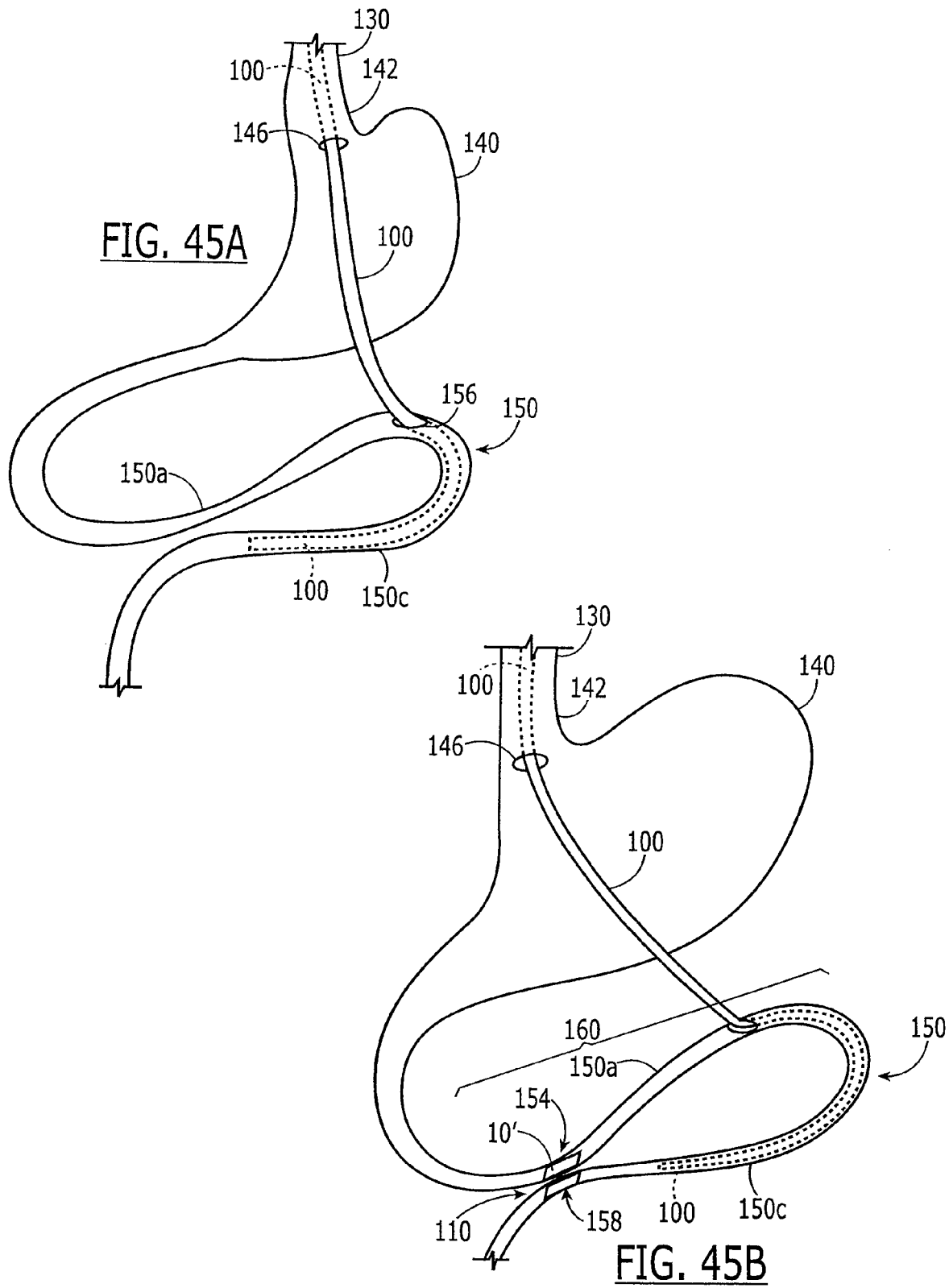
FIG. 45A is a schematic view of one exemplary embodiment of a method for treating obesity that includes forming openings in a stomach and an intestine and disposing an endoscope in a distal portion of the intestine.
FIG. 45B is a schematic view of the method of FIG. 45A that includes forming openings in a proximal portion and the distal portion of the intestine, forming an entero-entero anastomosis between the openings of the proximal and distal portions of the intestine, and deploying an anastomotic device in the entero-entero anastomosis.

As illustrated in FIG. 45A, an endoscope 100 is inserted into an esophagus 130 transorally. The endoscope 100 can travel through the esophagus 130, through the pylorus 142, and to a desired location in the stomach 140. A cutting device either associated with the endoscope 100 or inserted through the endoscope can be used to form an opening 146 through the stomach 140 wall. The cutting device can be any device configured to cut tissue, such as a needle or knife. Further, a second opening 156 can be formed in a distal portion of an intestine 160. This can be achieved by advancing the endoscope, or at least the cutting device, through the opening 146 and toward the intestine 160. The intestine 160 may need to be grasped and manipulated using graspers or other tools inserted laparoscopically, e.g., through a trocar cannula, through the abdominal wall and into the peritoneal cavity. The opening 156 in the intestine 160 can optionally be formed at the same time that the opening 146 in the stomach 140 is formed by positioning the intestine 160 adjacent to the stomach 140.

After forming the openings 146, 156 in the stomach 140 and the intestine 150, the endoscope 100 can continue through the intestine 150 to form openings 154, 158 in the portions 150a, 150c of the intestine 150 proximal and distal to opening 156, respectively, as shown in FIG. 45B. The endoscope 100, or at least a cutting device, can be directed to a desired location either toward the proximal or distal portion 150a, 150c of the intestine 150, and once the desired location is reached, the cutting device can be used to form openings 154, 158 in the respective proximal and distal portions 150a, 150c of the intestine 150. This may require one or more additional instruments be disposed in the body, e.g., laparoscopically, so that the proximal and distal portions 150a, 150c of the intestine 150 can be moved adjacent to each other. Similar to the formation of the openings 146, 156, the openings 154, 158 in the proximal and distal portions 154a, 154c of the intestine 150 can be formed at the same time, or alternatively, subsequent to each other. The formation of the two openings 154, 158 allows for the entero-entero anastomosis 110 to be formed. The entero-entero anastomosis 110 forms a pathway through which fluid can travel, and further, the formation of the entero-entero anastomosis 110 forms a loop 160 of the intestine 150.

Figure 45C:
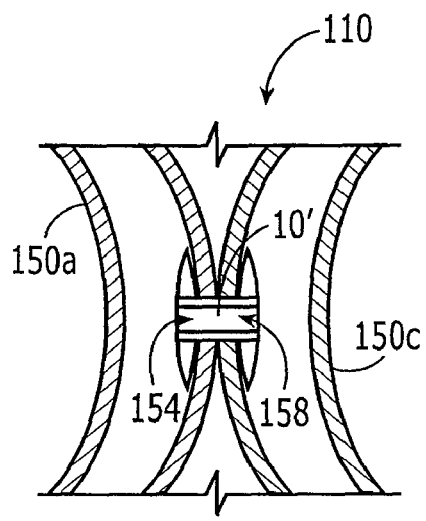
FIG. 45C is a close-up schematic view of the method of FIG. 45B taken at the location of the entero-entero anastomosis showing the anastomotic device deployed between the openings in the proximal and distal portions of the intestine.

Once the entero-entero anastomosis 110 is formed, an anastomotic device can be implanted between the two openings 154, 158. For example, anastomotic device 10' described above can be inserted through the mouth (not pictured), through the esophagus 130, through the stomach 140, through the openings 146, 156 in the stomach 140 and the intestine 150, respectively, through either the proximal or distal portions 150a, 150c of the intestine 150, and into the openings 154, 158. FIG. 45C illustrates the anastomotic device 10' disposed in the entero-entero anastomosis 110. In one exemplary embodiment the anastomotic device 10' is implanted by coupling the anastomotic device 10' to a delivery shaft which can be inserted through the endoscope 100 to position the device 10' between the two openings 154, 158, and to deploy the device 10' to engage the tissue surrounding the openings 154, 158 therebetween, thereby forming a pathway between the openings 154, 158. The anastomotic device 10' can also be delivered in a number of other different ways, such as, by way of non-limiting example, those discussed above with respect to the actuator 200 and other methods disclosed in the '131 Application.

Figure 45D:
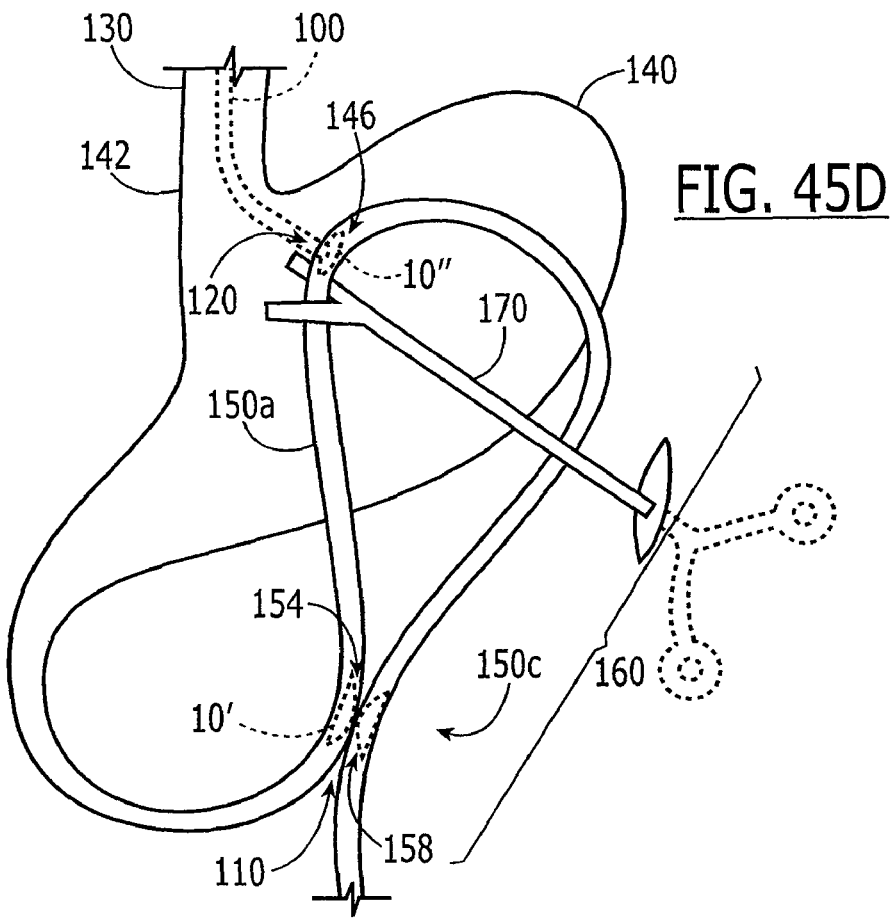
FIG. 45D is a schematic view of the method of FIG. 45B that includes retracting the endoscope from the distal portion of the intestine, forming a gastro-entero anastomosis between the openings in the stomach and the intestine and deploying an anastomotic device in the gastro-entero anastomosis.
Figure 45E:
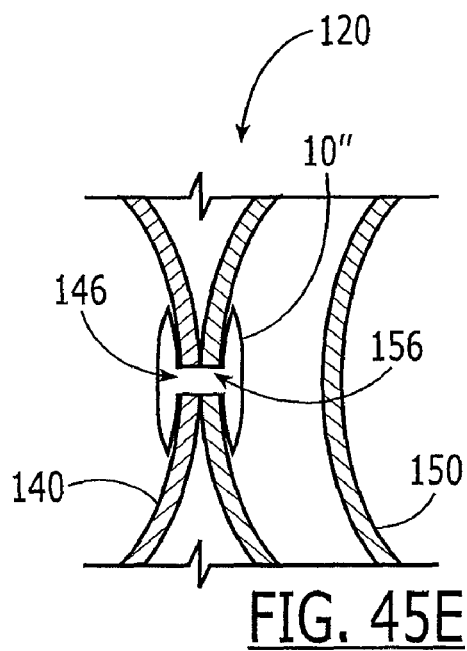
FIG. 45E is a close-up schematic view of the method of FIG. 45D taken at the location of the gastro-entero anastomosis showing the anastomotic device deployed between the openings in the stomach and the intestine.

After completing the entero-entero anastomosis 110, the endoscope 100 can be retracted back to the stomach 140 as shown in FIG. 45D. If the opening 156 in the intestine 150 is not adjacent to the opening 146 of the stomach 140, one or more instruments may be used to manipulate the intestine 150 to position the openings 146, 156 in alignment to facilitate the formation of the gastro-entero anastomosis 120. As previously indicated and as illustrated in FIG. 45D, a grasping tool 170 can be inserted into the body laparoscopically to grasp the intestine 150 and direct it to the desired location with respect to the stomach 140. In another embodiment a guide cable can be passed through or coupled to the intestine and the guide cable can subsequently be moved to guide the intestine to the desired location. Once the openings 146, 156 are adjacent to each other, the gastro-entero anastomosis 120 can be formed, e.g., using a second anastomotic device 10" deployed between the two openings 146, 156. The anastomotic device 10", which is similar to the anastomotic device 10 described above, can be inserted through the mouth (not pictured), through the esophagus 130, through the stomach 140, and into the openings 146, 156 of the stomach 140 and the intestine 150, respectively. FIG. 45E illustrates the anastomotic device 10" disposed in the gastro-entero anastomosis 120. The device 10" can be deployed as previously explained. Deploying the anastomotic device 10" forms a pathway through which fluid can travel.

Figure 45F:
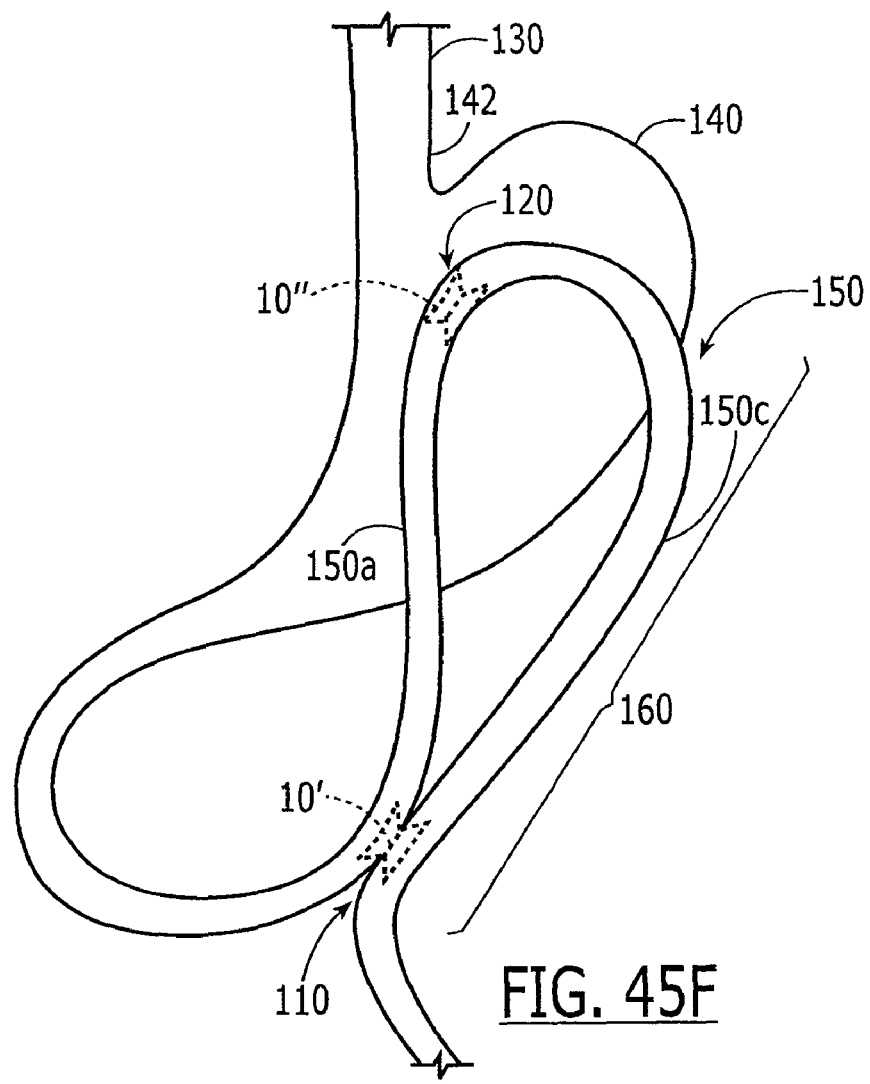
FIG. 45F is a schematic view of the method of FIGS. 45A-45E with the endoscope removed from the body and illustrating the resulting configuration of the stomach and the intestine.

While the delivery of the anastomotic devices 10', 10" can be done separately, a single device can be used for delivering both anastomotic devices 10', 10" such that first the entero-entero anastomosis 10' is delivered to form the entero-entero anastomosis 110 and then, as the device for delivering the anastomotic devices 10', 10" is retracted into the stomach, the gastro-entero anastomosis 10" is delivered to form the gastro-entero anastomosis 120. Once the procedure is complete, the endoscope 100 and other tools can be removed, leaving a configuration of the stomach 140 and the intestine 150 as is illustrated in FIG. 45F. More specifically, the gastro-entero anastomosis 120 is formed between the stomach 140 and the intestine 150 and has the anastomotic device 10" disposed therebetween and the loop 160 of the intestine 150 is formed between the proximal and distal portions 150a, 150c of the intestine. The entero-entero anastomosis 110 has the anastomotic device 10' disposed therebetween. This configuration allows fluid to travel to the distal portion 150c of the intestine: (a) directly from the gastro-entero anastomosis 120; (b) from the gastro-entero anastomosis 120, through the proximal portion 150a of the intestine 150, and through the entero-entero anastomosis 110; and/or (c) from the stomach 140, through the proximal portion 150a of the intestine 150, and through the entero-entero anastomosis 110.

In another embodiment, after the openings 146, 156 in the stomach 140 and the intestine 150 are formed and prior to either forming the openings 154, 158 in the proximal and distal portions 150a, 150c of the intestine 150 or deploying the anastomotic device 10', the gastro-entero anastomosis 120 can be formed and the anastomotic device 10" can be deployed in the openings 146, 156. When forming the gastro-entero anastomosis 120 before forming the entero-entero anastomosis 110, the endoscope 100 may need to be removed so that a second endoscope can be inserted in a similar fashion as the endoscope 100 was inserted and moved to a location for forming the entero-entero anastomosis 110. The second endoscope can be sized to fit through the anastomotic device 10", and thus is typically smaller than the first endoscope 100. The second endoscope and related cutting device can perform similar functions at the location of the entero-entero anastomosis 110 as the endoscope 100.

In still another embodiment, the openings 154, 158 in the proximal and distal portions 150*a*, 150*c* of the intestine 150 can be formed prior to forming either of the two openings 146, 156 in the stomach 140 and the intestine 150, for example by performing the endoscopic procedure transanally. In such an embodiment, first the entero-entero anastomosis 110 can be formed and then the gastro-entero anastomosis 120 can be formed. Alternatively, the gastro-entero anastomosis 120 can be formed before the entero-entero anastomosis 110. A person skilled in the art would understand how to apply the teachings described herein to engage in procedures for treating obesity which form the gastro-entero and entero-entero anastomoses in any order and beginning from any location.

The method can also include implanting a shunt to form a surrogate path to allow fluid to pass from a patient's esophagus to a patient's intestine through the gastro-entero anastomosis 120. The shunt can be coupled to the proximal end of the anastomotic device 10" disposed between the stomach 140 and the intestine 150, or alternatively, it can connect to or pass through the anastomotic device 10" so that it can deliver fluid to either or both of the proximal and distal portions 150*a*, 150*c* of the intestine 150. If coupled to the proximal end of the anastomotic device, the anastomotic device can be configured to deliver fluid to either or both of the proximal and distal portions 150*a*, 150*c* of the intestine 150. In one embodiment the shunt can be inserted prior to the formation of any anastomoses such that the shunt serves as a channel in which to perform the methods discussed herein. Upon completion of the formation of the anastomoses, the shunt can then be coupled to the proximal end of the anastomotic device located at the gastro-entero anastomosis. Insertion of the shunt can be done by way of a delivery shaft having the shunt coupled thereto. The delivery shaft can be inserted through the endoscope 100 and it can be manipulated to advance the delivery shaft, and thus the shunt, to a desired location. This may involve manipulating the delivery shaft, and thus the delivery device, around a tortuous pathway.

Figure 45G:
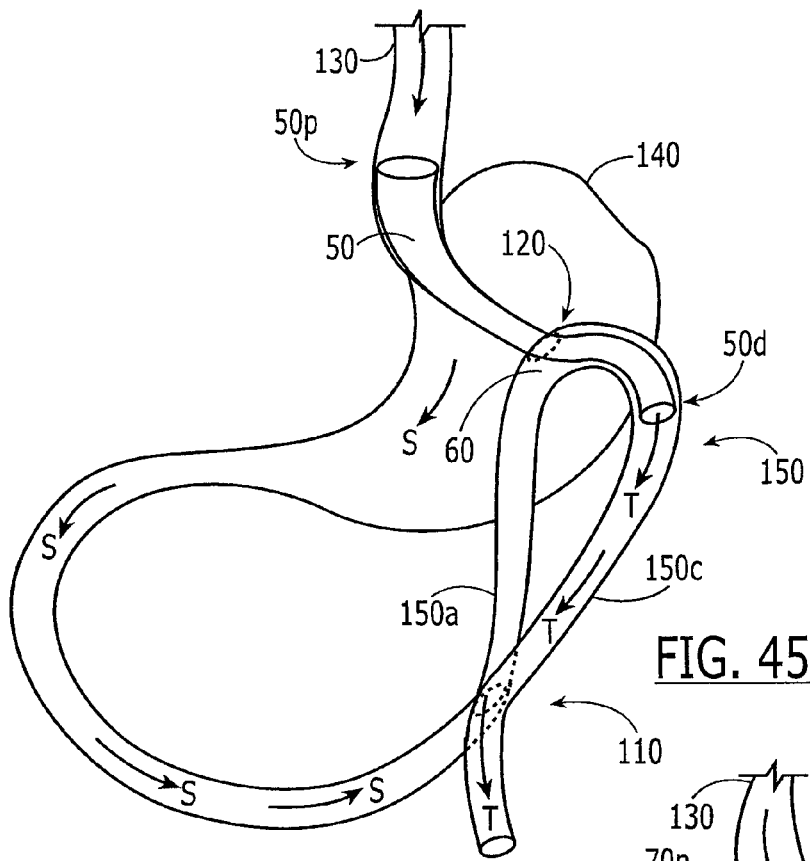
FIG. 45G is a schematic view of the shunt of FIG. 43 implanted in a stomach to deliver fluid from an esophagus to a gastro-entero anastomosis.

FIG. 45G illustrates one embodiment of a shunt implanted to deliver fluid in a single direction to the distal portion of the intestine. In this embodiment, the shunt 50 of FIG. 43 is used, thus the anastomotic device 60 is formed integrally with the shunt 50. In order to implant the shunt 50, the anastomotic device 60 is positioned in the openings 146, 156 and deployed as explained above, and the proximal end 50*p* of the shunt 50 is placed in communication with the esophagus while the distal end 50*d* of the shunt 50 is directed toward the distal portion 150*c* of the intestine 150. To assist with the delivery of the linear-shaped shunt 50, the distal end 50*d* can be configured to fold-up when disposed within an actuator, such as the actuator 200, or introducer sheath such that a sleeve thereof can be retracted to allow the distal end 50*d* of the linear-shaped shunt 50 to expand into place at a desired location. In the illustrated embodiment the distal end 50*d* is configured to direct fluid toward the distal portion 150*c* of the intestine 150, shown by the arrows T disposed therein. The arrows S indicate the flow of fluid from the stomach 140 toward the entero-entero anastomosis 110, which can include fluid that dissipates through the shunt if it is semi-permeable and fluid formed by the stomach, such as bile. Optionally, the distal end 50*d* can be configured to direct fluid toward the proximal portion 150*a* of the intestine 150, which because of the entero-entero anastomosis 110, is eventually directed toward the distal portion 150*c* of the intestine 150.

Figure 45H:
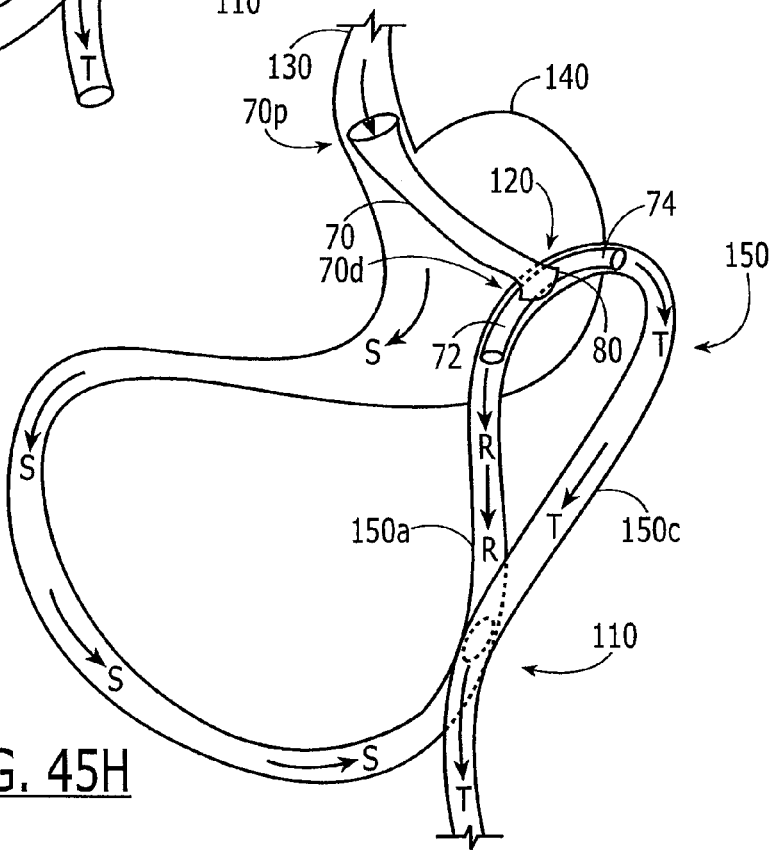
FIG. 45H is a schematic view of the shunt of FIG. 44 implanted in a stomach to deliver fluid from an esophagus to a gastro-entero anastomosis.

FIG. 45H illustrates a method for directing fluid from the esophagus into both the proximal and distal portions of the intestine using the Y-shaped shunt 70 of FIG. 44. The Y-shaped shunt 70 includes an anastomotic device 80 integrally formed thereon that is disposed at the gastro-entero anastomosis 120. More particularly, the Y-shaped shunt 70 is placed so that the anastomotic device 80 is disposed at the gastro-entero anastomosis 120, the proximal end 70*p* of the Y-shaped shunt 70 is positioned to receive fluid from the esophagus 130, and the distal end 70*d* of the Y-shaped shunt 70 is positioned to direct fluid in two directions toward the intestine 150. To assist with the delivery of the Y-shaped shunt 70, the distal end 70*d* can be configured to fold-up when disposed within an actuator, such as the actuator 200, or an introducer sheath such that a sleeve thereof can be retracted to allow the distal end 70*d* of the linear-shaped shunt 70 to expand into place at a desired location. In the illustrated embodiment the distal end 70*d* is configured to direct fluid toward both the proximal and distal portions 150*a*, 150*c* of the intestine, shown by the arrows R, T, respectively. The arrows S indicate the flow of fluid from the stomach 140 toward the entero-entero anastomosis 110, which can include fluid that dissipates through the shunt if it is semi-permeable and fluid formed by the stomach, such as bile. The fluid flowing toward the proximal and distal portions 150*a*, 150*c* will eventually flow toward the distal portion 150*c* of the intestine because the entero-entero anastomosis 110 causes the fluid flowing toward the proximal portion 150*a* to be directed to the distal portion 150*c*.

Upon the formation of either or both of the gastro-entero anastomosis and the entero-entero anastomosis, a seal test can be performed to insure that the connection between the two body components is secure. For example, in one embodiment one or more instruments for introducing a material into the anastomosis to test the seal between the two body components can be introduced. By way of a non-limiting example, the material can be methalyene blue. The methalyene blue can enter the anastomosis and the one or more instruments can allow an operator outside of the body to visualize whether the methalyene blue passes through the anastomosis without leaking into the stomach.

The methods and procedures discussed herein can also be altered or reversed. Thus, if after the procedures are performed a patient is having any difficulties, an operator can easily alter the procedure. Alterations of the procedure can include, but are not limited to, adjustments to the size, shape, material, type, and location of any of the shunt, the anastomotic devices, or any other instruments or tools that were used as part of the procedure. Likewise, if it is determined that a patient no longer needs the gastric bypass, the bypass can be removed. In one exemplary embodiment, the gastric bypass is removed by eliminating the surrogate path. This can be accomplished by removing the shunt from the system. The anastomoses can optionally remain, as removal of the shunt allows fluid to enter the stomach through the esophagus and be digested through the entero-entero anastomosis. This is a significant improvement over current procedures in which stapling off the stomach generally prevents the stomach from being used at a later period in time. While the anastomoses can remain, they can also be removed by removing the anastomotic devices and/or patching the openings through which the anastomotic devices were disposed.

By forming a gastro-entero anastomosis, fluid can pass from the esophagus, to the intestine, without entering the stomach. This allows food to be digested quicker and allows a patient to eat less. A patient eats less because receptors located in the wall of the stomach are adapted to sense the location of fluid, and based on the location of fluid, can signal to a patient's brain that the patient is full. It is the receptors that communicate hunger to a patient. A patient still gets enough fluid because the shunt can be configured to expand to allow enough fluid to enter the body to get enough vitamins, minerals, and nutrients to the patient. Because this procedure is adjustable and reversible, adjustments can be made to optimize the system for each individual patient. Further, the loop created by forming the entero-entero anastomosis provides multiple benefits. In embodiments in which the shunt is configured to deliver fluid in multiple directions, i.e., to the proximal and distal portions of the intestine, allowing the proximal portion to receive fluid from the shunt enables additional vitamins, minerals, and nutrients from the fluid to be absorbed by the body. Further, although the stomach is being bypassed by the shunt, in some embodiments the device can be semi-permeable, which means that fluid that dissipates through the shunt and into the stomach still has a pathway to enter the intestine. Still further, cells of a patient's stomach and liver generally produce a fluid, e.g. bile to digest food, so by forming the loop the fluid has a pathway to enter the intestine. Not providing a pathway for the fluid to exit the stomach can lead to other medical complications, such as a bowel obstruction.

Figure 46:
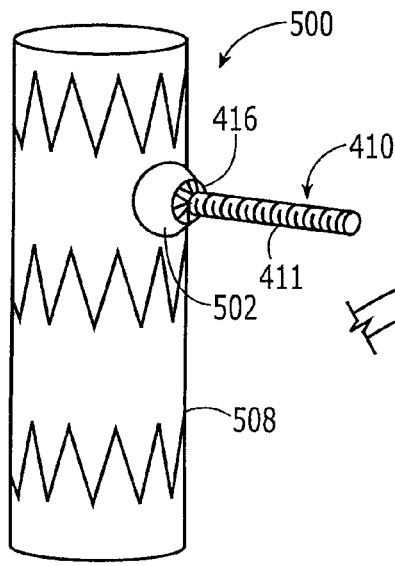
FIG. 46 is perspective view of one exemplary embodiment of an endovascular graft having the device of FIG. 11 associated therewith.
Figure 47:
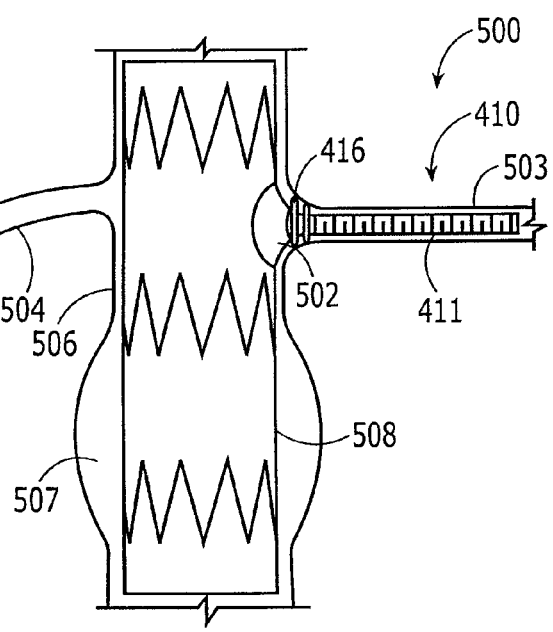
FIG. 47 is a side view of the graft of FIG. 46.

Anastomotic devices such as devices 10, 310, and 410 can also be used in other types of procedures beyond gastric bypass procedures. While some of these types of procedures are discussed in more detail in the '131 Application, in one embodiment the device 410 is used in conjunction with an endovascular graft for repair of an abdominal aortic aneurysm, as shown in FIGS. 46 and 47. The device 410 can be attached to an aneurysm graft 500 in a number of different ways, but in the illustrated embodiment a fenestration (not pictured) is formed in the aneurysm graft 500 and a dome 502 is placed or formed over the fenestration. The device 410 can be attached to the fenestration within the dome 502 using conventional mating techniques known in the art. The dome 502 can be constructed from a variety of materials, including materials that are both different and the same as the materials used to form the aneurysm graft 500. In one embodiment the aneurysm graft 500 and the dome 502 are formed of a biomaterial. The dome 502 provides maneuverability for accurate association of the device 410 with the aneurysm graft 500. For example, if the aneurysm graft 500 is used to treat a juxtarenal aortic aneurysm, the dome 502 can allow an operator the ability to find asymmetrical arteries, such as one or more renal arteries 504 attached to an aorta 506 having an aneurysm 507. Renal arteries 504 can be at different levels and in different planes with respect to the aorta 506, thus making accurate association between the device 410, the graft 500, and the renal arteries 504 difficult. The dome 502 can assist the operator in finding the renal arteries 504 and aligning the endovascular graft 500 with the renal arteries 504 for placement of a vascular conduit, such as covered stent 508, across the endovascular graft 500 into these branching arteries 504. Presently, location of such asymmetrical renal arteries 504 requires the construction of a customized fenestrated graft which is manufactured following extensive pre-planning using imaging technologies such as CAT and MRI scans.

The dome 502, however, can allow for off-the-shelf alignment of the endovascular graft 500 with side branch arteries 504 at various positions. Following alignment of the dome 502 in the endovascular graft 500 with the target side branch artery 504, a flexible vascular graft, such as illustrated tubular body 411 disposed in renal artery 503, can be anchored across the fenestration covered by the dome 502, for example by using wing technologies, illustrated as wings 416, as discussed with respect to devices 10, 310, and 410. While presently discussed with respect to the endovascular graft 500 being formed in the abdominal aorta position, it can also be used in other positions, for instance, in a thoracic aorta position. Likewise, while presently discussed with respect accessing renal arteries 504, any branch of an artery associated with any length of the aorta can be accessed using the teachings of the present disclosure.

Figure 48:
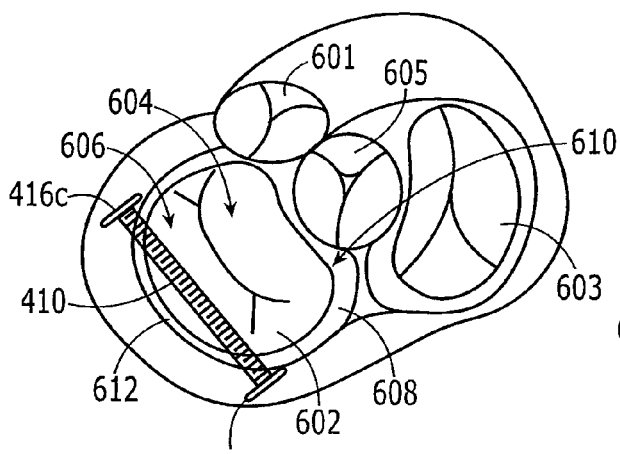
FIG. 48 is a schematic view of one exemplary embodiment of a heart valve repair having the device of FIG. 11 associated therewith.
Figure 49:
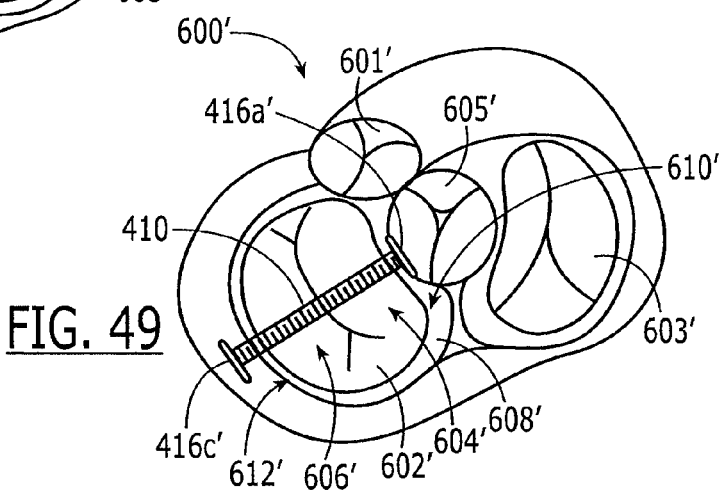
FIG. 49 is a schematic view of another exemplary embodiment of a heart valve repair having the device of FIG. 11 associated therewith.

By way of further non-limiting example, another procedure in which anastomotic devices such as devices 10, 310, and 410 can be used is to cinch tissues together. One example of this procedure is illustrated by FIGS. 48-49, in which a mitral annulus is cinched together to decrease its circumference and correct a leaking mitral valve (mitral regurgitation). As shown, a mitral valve 602 includes an anterior leaflet 604 and a posterior leaflet 606. The anterior and posterior leaflets 604, 606 are attached to an annulus 608. More specifically, the anterior and posterior leaflets 604, 606 are attached to a fibrous skeleton of a heart at an anterior annulus 610 and to a left ventricle at a posterior annulus 612. The leaflets 604, 606 are connected, primarily at their tips, by a chordae tendinae to papillary muscles, which originate from the left ventricle. Thus, the mitral apparatus is complex. Changes in one or a combination of its components can lead to significant mitral regurgitation, resulting in left ventricular dilation and worsening valvular incompetence. When there is disease of the leaflets 604, 606, most commonly due to myoxamatous degeneration, mitral regurgitation is classified as primary. When there is remodeling of the left ventricle but the leaflets 604, 606 are normal, mitral regurgitation is classified as secondary or functional.

Percutaneous repair of functional mitral regurgitation involves moving the posterior annulus 612 towards the anterior annulus 610 to increase leaflet 604, 606 coaptation. This may be achieved using anastomotic devices such as devices 10, 310, and 410. In the embodiment illustrated in FIG. 48, the device 410 is passed into tissue proximal to the annulus 608 of the mitral valve 602 of a heart 600 of a patient. For reference purposes, as illustrated, the heart 600 includes a pulmonary valve 601, a tricuspid valve 603, and an aorta 605. This can allow the device 410 to be placed circumferentially around the annulus 608 of the mitral valve. For example, the device 410 can be passed through the posterior mitral annulus 612 either under direct vision as in open surgery or under fluoroscopy (x-ray) control, or under echocardiography. Upon determining that the device 410 is in the correct position, the wings 416a, 416c can be formed and the tissue therebetween can be cinched together. The allows a diameter of the mitral annulus 608 to decrease in size, which in turn results in coaptation of the mitral valve leaflets 604, 606. Coaptation of the mitral valve leaflets 604, 606 can decrease the amount of mitral regurgitation through the valve 602 during systolic beating of the left ventricle. The degree of reduction of mitral regurgitation may be observed in real time during a percutaneous procedure by using, for example, echocardiography. Once the desired amount of coaptation of the leaflets 604, 606 is obtained, the delivery system used to deliver the device 410 can be disconnected from the device 410, as discussed with respect to other embodiments above.

Alternatively, as illustrated in FIG. 49, the device 410 can be passed across the mid-portion of the posterior annulus 612' and the anterior annulus 610' of the mitral valve 602' of the heart 600' of a patient and the degree of reduction of mitral regurgitation for the mitral valve leaflets 604', 606' can be observed under echocardiography or other imaging means in real time as the wings 416a, 416c are brought together. This can allow the device 410 to be placed transversally across the annulus 608' of the mitral valve. For reference purposes, as illustrated, the heart 600' includes a pulmonary valve 601', a tricuspid valve 603', and an aorta 605'.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for treating obesity, comprising:
   implanting an elongate member having proximal and distal deployable wings in the stomach by deploying the wings around an anastomosis formed between the stomach and a portion of the intestine such that the elongate member extends from the esophagus and through the anastomosis, the elongate member at least partially diverting fluid from the esophagus to the intestine thereby bypassing the stomach and at least a portion of the intestine proximal to the anastomosis.

2. The method of claim 1, further comprising:
   forming a second anastomosis between a proximal portion of the intestine and a distal portion of the intestine, wherein the proximal portion of the intestine is proximal to the anastomosis formed between the stomach and the intestine and the distal portion of the intestine is distal to the anastomosis formed between the stomach and the intestine.

3. The method of claim 1, further comprising reversing the method for treating obesity by removing the elongate member.

4. A method for forming a gastric bypass, comprising:
   forming an entero-entero anastomosis between first and second portions of an intestine such that a loop is formed in the intestine;
   forming a gastro-entero anastomosis between the loop and a stomach;
   implanting a shunt having proximal and distal deployable wings in the stomach and through the gastro-entero anastomosis such that fluid is at least partially directed from the esophagus, into the shunt, and then into the intestine by way of the gastro-entero anastomosis, thereby bypassing the stomach; and
   deploying the proximal and distal wings to engage tissue therebetween that is adjacent to the gastro-entero anastomosis.

5. The method of claim 4, wherein the loop includes first and second portions extending from the gastro-entero anastomosis, and wherein the shunt delivers fluid to only the first portion of the loop.

6. The method of claim 4, wherein the loop includes first and second portions extending from the gastro-entero anastomosis, and wherein the shunt delivers fluid to both the first and second portions of the loop.

7. The method of claim 4, wherein forming the entero-entero anastomosis includes implanting an anastomotic device at the entero-entero anastomosis.

8. The method of claim 7, further comprising adjusting a length of at least one of a connector extending between a proximal end and a distal end of at least one of the anastomotic devices and a connector extending between the proximal and distal wings.

9. The method of claim 8, wherein adjusting the length further comprises rotating a rod disposed between the respective proximal and distal ends and the proximal and distal wings.

10. The method of claim 8, wherein at least one of the anastomotic device and the shunt comprises a proximal tubular body and a distal tubular body, and adjusting the length comprises positioning the proximal tubular body along a portion of the distal tubular body.

11. The method of claim 7, wherein at least one of implanting an anastomotic device and implanting a shunt further comprises coupling at least a portion of an actuator used to deploy the anastomotic device or the shunt to the anastomotic device or shunt using sutures.

12. The method of claim 7, wherein at least one of implanting an anastomotic device and implanting a shunt further comprises coupling at least a portion of an actuator used to deploy the anastomotic device or the shunt to the anastomotic device or shunt by locking the anastomotic device or shunt to the actuator.

13. The method of claim 7, wherein at least one of implanting an anastomotic device and implanting a shunt further comprises breaking apart a portion of an actuator used to deploy the anastomotic device or the shunt to remove the actuator from the anastomotic device or the shunt.

14. The method of claim 4, wherein the proximal and distal wings are integrally formed on the shunt.

15. The method of claim 4, further comprising reversing the gastric bypass by removing the shunt.

16. The method of claim 4, wherein the gastro-entero anastomosis is formed prior to forming the entero-entero anastomosis and an anastomosis-forming device is passed through the gastro-entero anastomosis to form the entero-entero anastomosis.

17. The method of claim 4, wherein the entero-entero anastomosis is formed prior to forming the gastro-entero anastomosis and an anastomosis-forming device used to form the entero-entero anastomosis is used to form the gastro-entero anastomosis prior to removing the anastomosis-forming device from a surgical site.

18. The method of claim 4, further comprising inserting an endoscope through the shunt.

19. The method of claim 18, wherein implanting the shunt comprises manipulating the endoscope to advance a delivering shaft coupled to the shunt along a tortuous pathway.

20. The method of claim 4, wherein the shunt includes a one-way valve that inhibits acid reflux.

21. A method for forming a gastric bypass, comprising:
   positioning a portion of an intestine adjacent to a stomach;
   forming an anastomosis between the portion of the intestine and the stomach;
   positioning a shunt having an anastomotic device in the anastomosis to form a fluid connection between the portion of the intestine and the stomach, thereby
   forming a surrogate path from an esophagus to a distal portion of the intestine by way of the fluid connection such that fluid is at least partially directed from the esophagus to the intestine through the shunt thereby bypassing the stomach; and
   deploying the anastomotic device to engage tissue therebetween to secure the shunt in the anastomosis.

22. The method of claim 21, further comprising forming a connection between the distal portion of the intestine and a proximal portion of the intestine, wherein the proximal portion of the intestine is located proximal to the connection between the intestine and the stomach.

23. The method of claim 22, wherein the surrogate path extends to the proximal portion of the intestine by way of the connection between the intestine and the stomach.

24. The method of claim 22, wherein the connection between the proximal and distal portions of the intestine is formed by advancing a separate anastomotic device through the shunt having an anastomotic device, and implanting the separate anastomotic device between the proximal and distal portions of the intestine.

25. The method of claim 21, wherein the shunt is implanted by transorally advancing an endoscope having a delivery shaft coupled to the shunt disposed therearound.

26. The method of claim 21, further comprising reversing the gastric bypass by removing the surrogate path.

\* \* \* \* \*